(12) United States Patent
Toshima et al.

(10) Patent No.: US 7,374,285 B2
(45) Date of Patent: May 20, 2008

(54) EYEGLASS/CONTACT LENS POWER DETERMINING SYSTEM, AND ITS METHOD

(75) Inventors: Akio Toshima, Akashi (JP); Takehiko Yoshida, Higashiosaka (JP)

(73) Assignee: Vision Optic Co., Ltd., Osaka (JP)

( * ) Notice: Subject to any disclaimer, the term of this patent is extended or adjusted under 35 U.S.C. 154(b) by 601 days.

(21) Appl. No.: 10/480,341

(22) PCT Filed: Jun. 18, 2002

(86) PCT No.: PCT/JP02/06075

§ 371 (c)(1),
(2), (4) Date: Dec. 9, 2003

(87) PCT Pub. No.: WO03/000123

PCT Pub. Date: Jan. 3, 2003

(65) Prior Publication Data

US 2004/0174499 A1  Sep. 9, 2004

(30) Foreign Application Priority Data

Jun. 20, 2001 (JP) ............................. 2001-187154
Apr. 25, 2002 (JP) ............................. 2002-125049

(51) Int. Cl.
  *A01B 3/13* (2006.01)
(52) U.S. Cl. ...................................... 351/205; 351/246
(58) Field of Classification Search ................ 351/205, 351/246, 247, 200, 177
  See application file for complete search history.

(56) References Cited

U.S. PATENT DOCUMENTS 6,039,447 A * 3/2000 Minato ........................ 351/216
6,135,597 A * 10/2000 Minato ........................ 351/216

FOREIGN PATENT DOCUMENTS

| JP | 54-88195 | 7/1979 |
|---|---|---|
| JP | 64-49204 | 3/1989 |
| JP | 3-88502 | 9/1991 |
| JP | 8-215149 | 8/1996 |
| JP | 8-266473 | 10/1996 |
| JP | 10-85181 | 4/1998 |
| JP | 11-128168 | 5/1999 |

OTHER PUBLICATIONS

Longhui Liu et al., "Gradient Index Lens Model Eye", Kogaku, vol. 30, pp. 407-413, Jun. 2001.
Jiro Inoue, Mook No. 3, Jun. 1980., pp. 33-39.

* cited by examiner

*Primary Examiner*—Hung X. Dang
(74) *Attorney, Agent, or Firm*—Keating & Bennett, LLP

(57) ABSTRACT

A system and method for determining an eyeglass/contact lens power is provided, which can determine the power of an eyeglass/contact lens that is suitable for an individual. The eyeglass/contact lens power determination system (20) according to the present invention comprises inputting means (202) for entering information on the condition of a subject's eye, means (204) for determining an optical eyeball model corresponding to the information on the eye condition entered through the inputting means (202), and means (218) for selecting a lens power for verifying the focal power of an eyeglass/contact lens worn by the subject using the optical eyeball model determined by the optical eyeball model determining means to select a lens power.

42 Claims, 18 Drawing Sheets

Fig. 12

Lens power check

STEP 1 Entry of personal information and wearing conditions.

These items are important information to be used for determining the optimal lens power. Enter them correctly.

STEP1

◯ Name

[            ]

◯ Sex

○ Male  ○ Female

◯ Birthday

[2001 ▼] Year  [12 ▼] Month  [31 ▼] Day

◯ Height

[       ] cm

◀◀ Return            Next ▶▶

Measurement of far point vision

| 1 | 2 | 3 | 4 | 5 | No zone provides the viewing of three lines. |
|---|---|---|---|---|---|
| 10 | 9 | 8 | 7 | 6 | |

Click on the zone that provides the viewing of three lines. If no zone provides the viewing of three lines, click on the "No zone provides the viewing of three lines."

Measurement of near point distance

First, come as close to the screen as possible, and then go away to where you can clearly see the three lines. Measure the distance between the screen and your eye with a scale and then input the distance in cm.

EYEGLASS/CONTACT LENS POWER DETERMINING SYSTEM, AND ITS METHOD

TECHNICAL FIELD

The present invention relates to systems and methods for determining eyeglass/contact lens powers. In particular, the present invention relates to a system and method for determining eyeglass/contact lens powers, the system and method being preferably used with a remote subjective vision measurement system in which anyone can make subjective vision measurements or determine his or her eyeglass/contact lens power over networks.

BACKGROUND ART

Conventionally known as means for selecting eyeglass lenses are methods which utilize eyeball models. As the eyeball models, well known are the Gullstrand eyeball model and the Le-Grand eyeball model.

These eyeball models have been used entirely for the design and evaluation of eyeglass lenses. For the design of eyeglass lenses, one standard model prepared as an optical eye model would make it possible to design lenses having various powers for standard eyes. This is sufficiently enough for the design irrespective of the eye structure of a person because he/she can select among eyeglass lenses prepared every power of 0.25 D by actually wearing them, thereby ensuring that he/she finds eyeglass lenses suitable for correction. That is, there is a flexibility of selection.

These days, on the other hand, to measure uncorrected or corrected vision, one goes to see an ophthalmologist or has his/her sharpness of vision measured at eyeglass shops using their optometers.

Recently, for example, virtual malls are available over networks such as the Internet; however, any of the eyeglass shops available in these virtual malls provides no system for measuring the uncorrected and corrected vision on an on-line basis.

However, to solely determine the power of eyeglass lenses suitable for the eyes of an individual, an optical eyeball model such as the eyeball model assumed to be commonly applicable to everyone would cause significant error in optical calculation thereby making the determination impossible. The determination can be made only by constructing an optical eyeball model for each person.

Using the conventional eyeball models, as they are, will raise the following problems. That is, Since the conventional eyeball model is based on measurements made on eyes of people from Europe and the United States, they cannot be used for constructing a model having values close to those obtained by measuring living eyes of other races, e.g., Japanese people. For example, Japanese have a smaller radius of curvature of the cornea than do people from Europe and the United States.

A model is prepared based on an average of measurements.

Literatures show such data that the depth of the anterior chamber of the eye varies with age or the length of the eye axis is correlated with the degree of myopia for low degrees of nearsightedness. Thus, it is apparently necessary to construct an optical eyeball model according to the age and the degree of myopia of each individual.

Although the lens of the eye has a refractive index unevenly distributed, the average refractive index is used. The simplified double structure provided to the lens of the eye causes a significant error in tracking rays of light.

On the other hand, where difficulty is found in visiting medical care providers or eyeglass shops such as due to the time required and the distance traveled for the visit, there has been a need for implementing a system which enables one to remotely measure his/her sharpness of vision over the Internet.

In particular, one's currently wearing eyeglasses or contact lenses may provide more blurred viewing than before. In this case, it would be very convenient if one can remotely measure his/her uncorrected and corrected vision in order to determine whether he/she needs to buy new eyeglasses or contact lenses.

It is therefore a principal object of the present invention to provide a system and method for determining an eyeglass/contact lens power suitable for an individual.

DISCLOSURE OF THE INVENTION

The invention set forth in claim 1 provides a system for determining an eyeglass/contact lens power, the system comprising: inputting means for entering information on a condition of a subject's eye; means for determining an optical eyeball model corresponding to the information on the eye condition entered through the inputting means; and means for selecting a lens power for verifying a focal power of an eyeglass/contact lens worn by the subject using the optical eyeball model determined by the optical eyeball model determining means. In this case, an optical eyeball model unique to the subject is constructed to select a lens power using the optical eyeball model. This makes it possible to select the lens power of the eyeglass/contact lens which is optimally suitable for the subject.

The invention set forth in claim 2 provides the system for determining an eyeglass/contact lens power according to claim 1, wherein the inputting means includes means for displaying an astigmatic axis measurement chart to measure an astigmatic axis. This makes it possible to know the astigmatic axis of the subject.

The invention set forth in claim 3 provides the system for determining an eyeglass/contact lens power according to claim 1 or 2, wherein the inputting means includes means for displaying a far point vision measurement chart to measure far point vision. This makes it possible to know the far point vision of the subject.

The invention set forth in claim 4 provides the system for determining an eyeglass/contact lens power according to any one of claims 1 to 3, wherein the inputting means includes means for displaying a near point distance measurement chart to measure a near point distance. This makes it possible to know the near point distance of the subject.

The invention set forth in claim 5 provides the system for determining an eyeglass/contact lens power according to claim 3 or 4, wherein the inputting means has means for calculating a far point distance from the far point vision measured. In this case, the far point distance is calculated from the far point vision to determine an optical eyeball model in accordance with the resulting value. This makes it possible for the subject to select the lens power of his/her eyeglass/contact lens, which is optimally suitable for the subject, by measuring the far point vision without actually measuring the far point distance. This preferably allows the subject to select the lens power of his/her eyeglass/contact lens in a small room or the like.

The invention set forth in claim 6 provides the system for determining an eyeglass/contact lens power according to claim 5, wherein the inputting means has means for determining an approximate lens power from the far point distance calculated. In this case, the age, the near point distance, and the far point distance of the subject are entered to thereby determine his/her optical eyeball model. This makes it possible for the subject to select the lens power of his/her eyeglass/contact lens, which is optimally suitable for the subject, by entering the age, the near point distance, and the far point distance of the subject.

The invention set forth in claim 7 provides the system for determining an eyeglass/contact lens power according to any one of claims 1 to 6, wherein the optical eyeball model simulates each layer of an anterior cortex, a nucleoplasm, and a posterior cortex of the lens of the eye using a combination of plurality of lenses, respectively. In this case, it is possible to construct an optical eyeball model that is similar to the actual eyeball structure. This also makes it possible to select the lens power of the eyeglass/contact lens which is suitable for the subject.

The invention set forth in claim 8 provides the system for determining an eyeglass/contact lens power according to any one of claims 1 to 7, wherein the optical eyeball model has a characteristic that a refractive index of each of the lenses simulating the lens of the eye is decreased with a distance from the center of the lens. In this case, it is also possible to construct an optical eyeball model that is similar to the actual eyeball structure. This also makes it possible to select the lens power of the eyeglass/contact lens which is suitable for the subject.

The invention set forth in claim 9 provides the system for determining an eyeglass/contact lens power according to claim 8, wherein the optical eyeball model has a refractive index distribution characteristic that the refractive index of each of the lenses simulating the lens of the eye is expressed by (a refractive index at the center of the lens)−((the square of a straight distance from the lens center)/(a refractive index distribution coefficient)). In this case, it is also possible to construct an optical eyeball model that is similar to the actual eyeball structure. This also makes it possible to select the lens power of the eyeglass/contact lens which is suitable for the subject.

The invention set forth in claim 10 provides the system for determining an eyeglass/contact lens power according to any one of claims 7 to 9, wherein the refractive index distribution coefficient of each lens simulating the lens of the eye is decreased with the distance from the center of the plurality of lenses in a direction of the optical axis simulating the lens of the eye to the direction of the optical axis. In this case, it is also possible to construct an optical eyeball model that is similar to the actual eyeball structure. This also makes it possible to select the lens power of the eyeglass/contact lens which is suitable for the subject.

The invention set forth in claim 11 provides the system for determining an eyeglass/contact lens power according to any one of claims 7 to 10, wherein the optical eyeball model calculates optical dimensions using a power distribution coefficient describing the distribution of accommodation power per unit length of each lens simulating the lens of the eye. In this case, it is also possible to construct an optical eyeball model that takes into account the accommodation power of the actual eyeball. This also makes it possible to select the lens power of the eyeglass/contact lens which is suitable for the subject.

The invention set forth in claim 12 provides the system for determining an eyeglass/contact lens power according to any one of claims 1 to 11, wherein the means for determining an optical eyeball model determines a starting optical eyeball model in accordance with an age of the subject and information on the eye such as an approximate lens power. In this case, an optical eyeball model is selected in accordance with the age of the subject and the information on the eye such as the approximate lens power to thereby select the lens power of the eyeglass/contact lens which is optimally suitable for the subject. This makes it possible to select the lens power of the eyeglass/contact lens, which is optimally suitable for the subject, only by the subject entering his/her age and information required for calculating the approximate lens power or the like.

The invention set forth in claim 13 provides the system for determining an eyeglass/contact lens power according to any one of claims 1 to 12, wherein the means for determining an optical eyeball model has means for verifying validity of the optical eyeball model at a given accommodation point between the near point distance and the far point distance of the subject entered. In this case, determined is an optical eyeball model which more closely simulates the eyeball of the subject. This also makes it possible to select the lens power of the eyeglass/contact lens which is suitable for the subject.

The invention set forth in claim 14 provides the system for determining an eyeglass/contact lens power according to claim 13, wherein the given accommodation point between the near point distance and the far point distance of the subject entered includes an accommodation midpoint calculated from the near point distance and the far point distance of the subject. This makes it possible to equally distribute the accommodation power to the respective strained and relaxed sides.

The invention set forth in claim 15 provides the system for determining an eyeglass/contact lens power according to claim 13 or 14, wherein the means for determining an optical eyeball model employs a radius of curvature and an eccentricity of an aspherical surface as parameters to perform automatic aberration correction processing. In this case, the automatic aberration correction processing is performed in a short period of time. This makes it possible to quickly select the lens power of the eyeglass/contact lens which is optimally suitable for the subject.

The invention set forth in claim 16 provides the system for determining an eyeglass/contact lens power according to any one of claims 1 to 15, wherein the means for determining an optical eyeball model includes means for verifying validity of the optical eyeball model at an accommodation limit on a near point side and/or a far point side. This also makes it possible to select the lens power of the eyeglass/contact lens which is suitable for the subject.

The invention set forth in claim 17 provides the system for determining an eyeglass/contact lens power according to any one of claims 1 to 16, wherein the means for determining an optical eyeball model displays an image of the optical eyeball model determined. This makes it possible for the subject to view how his/her optical eyeball model has been determined.

The invention set forth in claim 18 provides the system for determining an eyeglass/contact lens power according to any one of claims 1 to 17, wherein the means for selecting a lens power has a function to verify the focal power at a single distance or a plurality of distances defined according to usage. In this case, the focal power is calculated at three distances according to actual usage. This allows the subject to readily determine whether the selected lens is suitable for his/her usage.

The invention set forth in claim 19 provides the system for determining an eyeglass/contact lens power according to any one of claims 1 to 18, wherein the means for selecting a lens power has a function to verify by comparison the focal power of the optical eyeball model for an uncorrected eye. In this case, the focal conditions of the uncorrected and corrected eyes are verified by comparison, thereby making clear what kind of changes may occur when the subject wears the eyeglasses or the contact lenses. This also makes it possible to accurately select appropriate lenses.

The invention set forth in claim 20 provides the system for determining an eyeglass/contact lens power according to any one of claims 1 to 19, wherein the means for selecting a lens power includes means for calculating a sharpness score indicative of the degree of blurring in a visual image viewed by an optical eyeball model. In this case, the focal conditions of the uncorrected and corrected eyes are verified by comparison, thereby making clear what kind of changes have occurred. This also makes it possible to accurately select appropriate lenses.

The invention set forth in claim 21 provides the system for determining an eyeglass/contact lens power according to any one of claims 1 to 20, wherein the means for selecting a lens power includes means for presenting a simulated visual image viewed by the optical eyeball model. In this case, it is possible to view and check directly on a screen the degree of blurring in an image viewed by the subject. This allows the subject to easily select lenses.

The invention set forth in claim 22 provides a method for determining an eyeglass/contact lens power, the method comprising steps of collecting information on the conditions of an eye of a subject; determining an optical eyeball model corresponding to the information on the conditions of the eye collected in the collecting step; and selecting a lens power by verifying a focal power of an eyeglass/contact lens worn by the subject using the optical eyeball model determined in the step for determining an optical eyeball model. In this case, an optical eyeball model unique to the subject is constructed to select a lens power using the optical eyeball model. This makes it possible to select the lens power of the eyeglass/contact lens which is optimally suitable for the subject.

The invention set forth in claim 23 provides the method for determining an eyeglass/contact lens power according to claim 22, wherein the collecting step includes a step of displaying an astigmatic axis measurement chart to measure an astigmatic axis. This makes it possible to know the astigmatic axis of the subject.

The invention set forth in claim 24 provides the method for determining an eyeglass/contact lens power according to claim 22 or 23, wherein the collecting step includes a step of displaying a far point vision measurement chart to measure far point vision. This makes it possible to know the far point vision of the subject.

The invention set forth in claim 25 provides the method for determining an eyeglass/contact lens power according to any one of claims 22 to 24, wherein the collecting step includes a step of displaying a near point distance measurement chart to measure a near point distance. This makes it possible to know the near point distance of the subject.

The invention set forth in claim 26 provides the method for determining an eyeglass/contact lens power according to claim 24 or 25, wherein the collecting step has a step of calculating a far point distance from the far point vision measured. This makes it possible for the subject to select the lens power of his/her eyeglass/contact lens, which is optimally suitable for the subject, by measuring the far point vision without actually measuring the far point distance. This preferably allows the subject to select the lens power of his/her eyeglass/contact lens in a small room or the like.

The invention set forth in claim 27 provides the method for determining an eyeglass/contact lens power according to claim 26, wherein the collecting step has a step of determining an approximate lens power from the far point distance calculated. In this case, the age, the near point distance, and the far point distance of the subject are entered to thereby determine his/her optical eyeball model. This makes it possible for the subject to select the lens power of his/her eyeglass/contact lens, which is optimally suitable for the subject, by entering the age, the near point distance, and the far point distance of the subject.

The invention set forth in claim 28 provides the method for determining an eyeglass/contact lens power according to any one of claims 22 to 27, wherein the optical eyeball model simulates each layer of an anterior cortex, a nucleoplasm, and an posterior cortex of the lens of the eye using a combination of plurality of lenses, respectively. In this case, it is possible to construct an optical eyeball model that is similar to the actual eyeball structure. This also makes it possible to select the lens power of the eyeglass/contact lens which is suitable for the subject.

The invention set forth in claim 29 provides the method for determining an eyeglass/contact lens power according to any one of claims 22 to 28, wherein the optical eyeball model has a characteristic that a refractive index of each of the lenses simulating the lens of the eye is decreased with a distance from the center of the lens. In this case, it is also possible to construct an optical eyeball model that is similar to the actual eyeball structure. This also makes it possible to select the lens power of the eyeglass/contact lens which is suitable for the subject.

The invention set forth in claim 30 provides the method for determining an eyeglass/contact lens power according to claim 29, wherein the optical eyeball model has a refractive index distribution characteristic that the refractive index of each of the lenses simulating the lens of the eye is expressed by (a refractive index at the center of the lens)−((the square of a straight distance from the lens center)/(a refractive index distribution coefficient)). In this case, it is also possible to construct an optical eyeball model that is similar to the actual eyeball structure. This also makes it possible to select the lens power of the eyeglass/contact lens which is suitable for the subject.

The invention set forth in claim 31 provides the method for determining an eyeglass/contact lens power according to any one of claims 28 to 30, wherein the refractive index distribution coefficient of each lens simulating the lens of the eye is decreased with the distance from the center of the plurality of lenses in a direction of the optical axis simulating the lens of the eye to the direction of the optical axis. In this case, it is also possible to construct an optical eyeball model that is similar to the characteristics of the actual eyeball. This also makes it possible to select the lens power of the eyeglass/contact lens which is suitable for the subject.

The invention set forth in claim 32 provides the method for determining an eyeglass/contact lens power according to any one of claims 28 to 31, wherein the optical eyeball model calculates optical dimensions using a power distribution coefficient describing the distribution of accommodation power per unit length of each lens simulating the lens of the eye. In this case, it is also possible to construct an optical eyeball model that takes into account the accommodation power of the actual eyeball. This also makes it possible to select the lens power of the eyeglass/contact lens which is suitable for the subject.

The invention set forth in claim 33 provides the method for determining an eyeglass/contact lens power according to any one of claims 22 to 32, wherein the step of determining an optical eyeball model determines a starting optical eyeball model in accordance with an age of the subject and information on the eye such as an approximate lens power. In this case, an optical eyeball model is selected in accordance with the age of the subject and the information on the eye such as the approximate lens power to thereby select the lens power of the eyeglass/contact lens which is optimally suitable for the subject. This makes it possible to select the lens power of the eyeglass/contact lens, which is optimally suitable for the subject, only by the subject entering his/her age and information required for calculating the approximate lens power or the like.

The invention set forth in claim 34 provides the method for determining an eyeglass/contact lens power according to any one of claims 22 to 33, wherein the step of determining an optical eyeball model has a step of verifying validity of the optical eyeball model at a given accommodation point between the near point distance and the far point distance of the subject entered. In this case, determined is an optical eyeball model which more closely simulates the eyeball of the subject. This also makes it possible to select the lens power of the eyeglass/contact lens which is suitable for the subject.

The invention set forth in claim 35 provides the method for determining an eyeglass/contact lens power according to claim 34, wherein the given accommodation point between the near point distance and the far point distance of the subject entered includes an accommodation midpoint calculated from the near point distance and the far point distance of the subject. This makes it possible to equally distribute the accommodation power to the respective strained and relaxed sides.

The invention set forth in claim 36 provides the method for determining an eyeglass/contact lens power according to claim 34 or 35, wherein the step of determining an optical eyeball model employs a radius of curvature and an eccentricity of an aspherical surface as parameters to perform automatic aberration correction processing. In this case, the automatic aberration correction processing is performed in a short period of time. This makes it possible to quickly select the lens power of the eyeglass/contact lens which is optimally suitable for the subject.

The invention set forth in claim 37 provides the method for determining an eyeglass/contact lens power according to any one of claims 22 to 36, wherein the step of determining an optical eyeball model includes a step of verifying validity of the optical eyeball model at an accommodation limit on a near point side and/or a far point side. This also makes it possible to select the lens power of the eyeglass/contact lens which is suitable for the subject.

The invention set forth in claim 38 provides the method for determining an eyeglass/contact lens power according to any one of claims 22 to 37, wherein the step of determining an optical eyeball model displays an image of the optical eyeball model determined. This makes it possible for the subject to view how his or her optical eyeball model has been determined.

The invention set forth in claim 39 provides the method for determining an eyeglass/contact lens power according to any one of claims 22 to 38, wherein the step of selecting a lens power has a step of verifying the focal power at a single distance or a plurality of distances defined according to usage. In this case, the focal power is calculated at three distances according to actual usage. This allows the subject to readily determine whether the selected lens is suitable for his/her usage.

The invention set forth in claim 40 provides the method for determining an eyeglass/contact lens power according to any one of claims 22 to 39, wherein the step of selecting a lens power has a step of verifying by comparison the focal power of the optical eyeball model for an uncorrected eye. In this case, the focal conditions of the uncorrected and corrected eyes are verified by comparison, thereby making clear what kind of changes may occur when the subject wears the eyeglasses or the contact lenses. This also makes it possible to accurately select appropriate lenses.

The invention set forth in claim 41 provides the method for determining an eyeglass/contact lens power according to any one of claims 22 to 40, wherein the step of selecting a lens power includes a step of calculating a sharpness score indicative of the degree of blurring in a visual image viewed by an optical eyeball model. In this case, the focal conditions of the uncorrected and corrected eyes are verified by comparison, thereby making clear what kind of changes have occurred. This also makes it possible to accurately select appropriate lenses.

The invention set forth in claim 42 provides the method for determining an eyeglass/contact lens power according to any one of claims 22 to 41, wherein the step of selecting a lens power includes a step of presenting a simulated visual image viewed by the optical eyeball model. In this case, it is possible to view and check directly on a screen the degree of blurring in an image viewed by the subject. This allows the subject to easily select lenses.

The aforementioned objects, other objects, features, and advantages of the present invention will be better understood from the following detailed descriptions to be made with reference to the drawings in accordance with the embodiments.

BRIEF DESCRIPTION OF THE DRAWINGS

FIG. 12 is a view illustrating an example of a representation of an individual information input window;

BEST MODE FOR CARRYING OUT THE INVENTION

Figure 1:
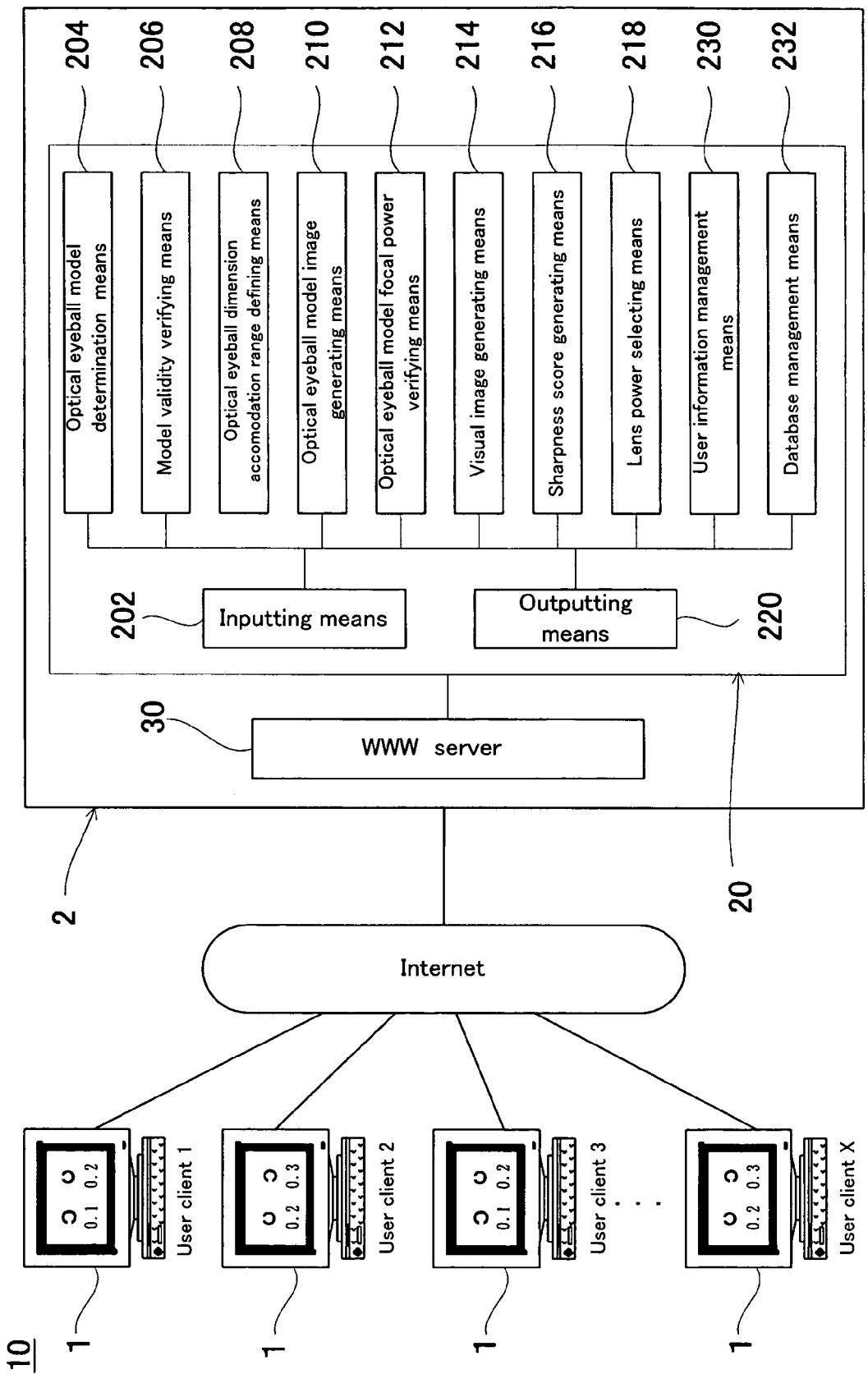
FIG. 1 is a view illustrating an exemplary configuration of a remote subjective vision measurement system comprising an eyeglass/contact lens power determination server incorporating an eyeglass/contact lens power determination system according to an embodiment of the present invention.

FIG. 1 is a view illustrating an exemplary configuration of a remote subjective vision measurement system comprising an eyeglass/contact lens power determination server incorporating an eyeglass/contact lens power determination system according to an embodiment of the present invention.

As shown in FIG. 1, the remote subjective vision measurement system 10 comprises hardware of user clients 1 and an electronic service center 2. These are physically connected to each other via networks.

The following descriptions will be given assuming that the network connecting between the user clients 1 and the electronic service center 2 is the Internet.

The remote subjective vision measurement system 10, comprising the electronic service center 2, can construct an optical eyeball model unique to a subject to determine the optimal power for the subject in accordance with the age and wearing conditions entered at the user client 1 and the vision measurement data indicative of the degree of nearsightedness, farsightedness and astigmatism.

The electronic service center 2 comprises an eyeglass/contact lens power determination server 20, which has inputting means 202, optical eyeball model determination means 204, model validity verifying means 206, optical eyeball dimension accommodation range defining means 208, optical eyeball model image generating means 210, optical eyeball model focal power verifying means 212, visual image generating means 214, sharpness score generating means 216, lens power selecting means 218, outputting means 220, user information management means 230, and database management means 232, and a WWW (World Wide Web) server 30.

More specifically, the electronic service center 2 comprises information processing devices including, for example, personal computers, workstations, and servers.

The databases controlled by the database management means 232 are stored in a storage device such as a magnetic disc device or an optical disc device.

The electronic service center 2 is connected to the user clients 1 via a wide area computer network (the Internet).

The WWW server 30 provides a homepage that is used as an interface across which the user client 1 accesses the database management means 232 or the like in the electronic service center 2.

Furthermore, the WWW server 30 has user authentication means (not shown) which uses a password/identifier (ID) to verify whether an user has been authorized to have a right to register with or request the viewing of the databases managed by the database management means 232.

The lens power selecting means 218 verifies the optical performance of an eyeglass/contact lens worn by a subject to select the lens power.

The inputting means 202 is designed to receive information on the eyes of a subject such as the wearing conditions, the age, the near point distance, and the far point distance of the subject. Furthermore, the inputting means 202 comprises astigmatic axis measuring means for displaying an astigmatic axis measurement chart to measure the astigmatic axis; far point vision measuring means for displaying a far point vision measurement chart used with the measurement of far point vision to measure a far point distance; near point distance measuring means for displaying a near point distance measurement chart to measure a near point distance; far point distance calculating means for calculating a far point distance from the far point vision; and means for determining an approximate lens power from the far point distance or the like.

The optical eyeball model determination means 204 is designed to determine a starting optical eyeball model in accordance with the age of a subject and information on the eye such as the approximate lens power. The optical eyeball model determination means 204 is designed to determine an optical eyeball model in accordance with such eyeball optical dimensions that the focal power of the eyeball of a subject is optimized at the accommodation midpoint calculated from the near point distance and the far point distance of the subject. This embodiment is designed to determine the optical eyeball model at the accommodation midpoint based on the fact that a condition can be provided, in which the eyeball is strained to its limit or relaxed to its limit, by equally distributing the accommodation power of the eyeball of the subject to the strained side or the relaxed side.

Figure 2:
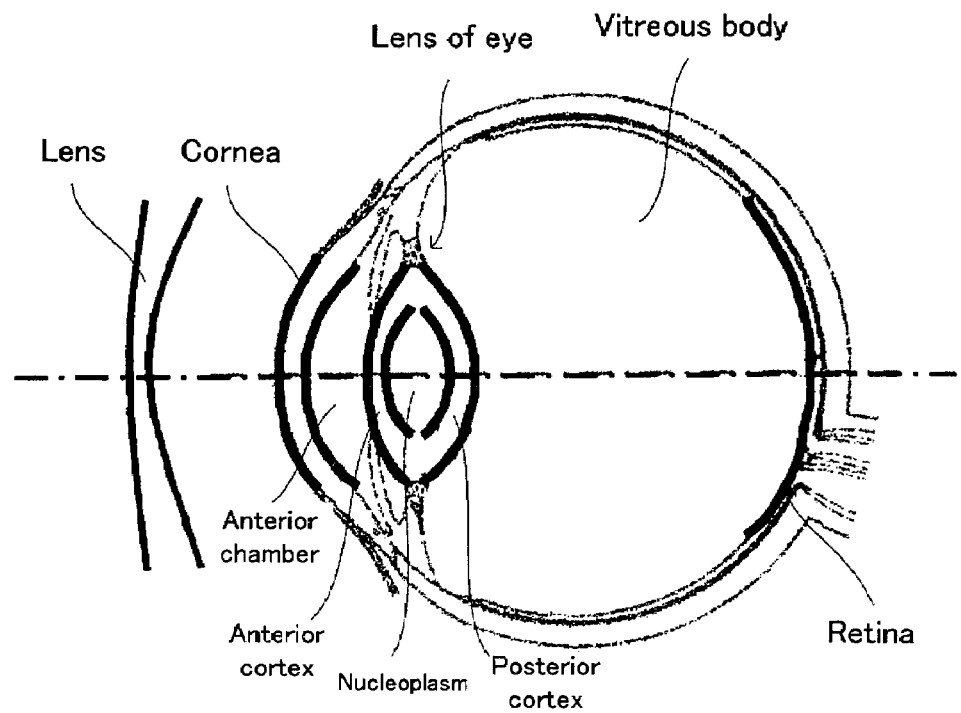
FIG. 2 is a cross-sectional pictorial view illustrating an eyeball.
Figure 3:
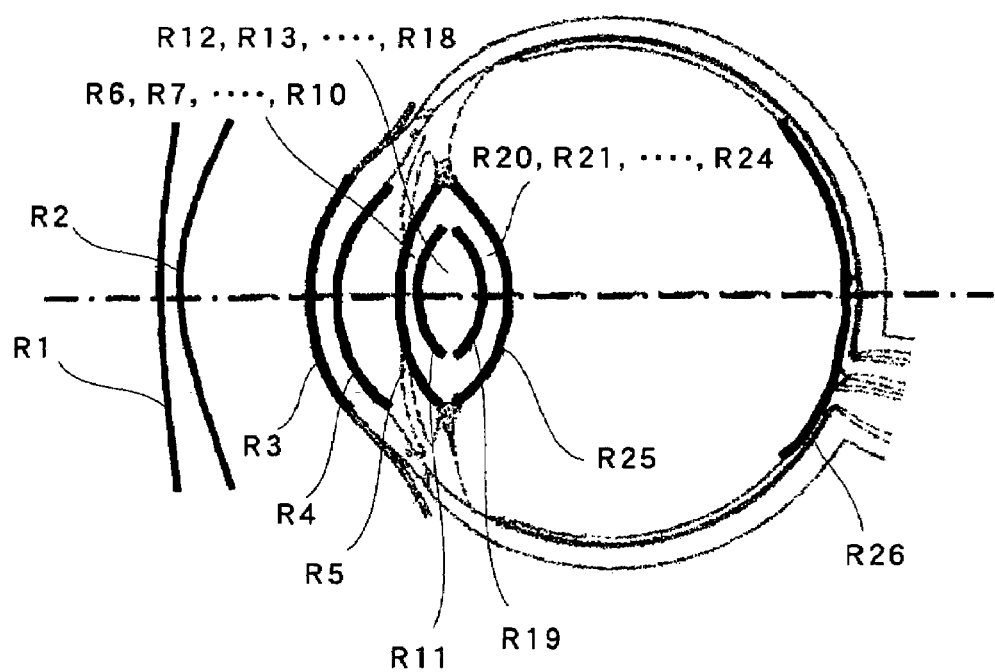
FIG. 3 is a cross-sectional pictorial view illustrating an optical eyeball model.

Now, the optical eyeball model to be constructed according to this embodiment will be explained below. In the optical eyeball model, a human eye and a lens such as an eyeglass/contact lens, as shown in FIG. 2, are configured as an optical system numerical model from a plurality of lenses as shown in FIG. 3. As shown in FIG. 3, the optical eyeball model comprises light-ray refracting elements of the eyeball such as the cornea, the anterior chamber, the lens of the eye, and the vitreous body, and the retina or an optically evaluated surface. An optical eyeball model is constructed with respect to these elements in accordance with the following optical dimensions.

Eyeglass/contact lens: the radius of curvature R1 of the lens front surface, the thickness, the refractive index, and the radius of curvature R2 of the lens rear surface Cornea: the radius of curvature R3 of the front surface, the thickness, the refractive index, and the radius of curvature R4 of the rear surface Anterior chamber: the thickness and the refractive index Lens of the eye: the radius of curvature (the radii of curvature R5, R6, R7, R8, R9, R10, and R11 on each boundary surface of lenses in six layers simulating the anterior cortex) and the thickness of the anterior cortex; the radius of curvature (the radii of curvature R11, R12, R13, R14, R15, R16, R17, R18, and R19 on each boundary surface of lenses in eight layers simulating the nucleoplasm) and the thickness of the nucleoplasm; and the radius of curvature (the radii of curvature R19, R20, R21, R22, R23, R24, and R25 on each boundary surface of lenses in six layers simulating the posterior cortex) and the thickness of the posterior cortex and their respective refractive indices Vitreous body: the refractive index and the thickness Retina: Radius of curvature R26

The aforementioned optical dimensions are different from each other depending on the age and the accommodation capability of the eye of each individual. However, in this embodiment, an optical eyeball model is pre-constructed as a standard pattern with respect to values from living body measurement data on Japanese people and those from literature data.

Now, shown below is an example of literature data applicable to the construction of an optical eyeball model.

(i) Concerning the Depth of the, Anterior Chamber

According to "Study on the depth of anterior chamber" by Katsuo Aizawa, Japanese Ophthalmological Society Journal Vol.62, No. 11 (1958), the relationship between the depth of the anterior chamber and the age varies as follows:

3.66 mm for ages from 8 to 15,
3.71 mm for ages from 16 to 30,
3.51 mm for ages from 31 to 51, and
3.18 mm for ages from 51 to 77.

That is, the study tells that the depth of the anterior chamber tends to gradually increase as the body grows from the youth and reach the maximum level when the body has grown up, thereafter gradually decrease as the body deteriorates.

(ii) Concerning the Length of the Eye Axis

According to "Study No. 1 on the essence of nearsightedness" by Tsutomu Sato, et al, Japanese Ophthalmological Society Journal Vol.63, No. 7 (1959), for the low degree of nearsightedness, the length of the eye axis gradually increases as the degree of myopia becomes higher, showing a strong correlation therebetween.

(iii) Concerning the Weight of the Lens of the Eye

According to "The eye" by Davson Hugh (1909-) and Graham L. T. Jr., New York; London Academic Press, the weight of the lens of the eye only increases with advancing age as follows:

174 mg for ages from 20 to 39,
204 mg for ages from 40 to 59, and
266 mg for ages from 80 to 99.

(iv) Concerning the Thickness and Diameter of the Lens of the Eye

According to Complete Collection of New Clinical Ophthalmology 3A, by Hiroshi Ichikawa, et al, 1993, KANEHARA & CO., LTD, the thickness and diameter of the lens of the eye increases with advancing age.

The optical eyeball model that has been constructed by applying the values from the aforementioned literatures and those of the living body measurement data is used as the starting optical eyeball model. The starting optical eyeball model is not constructed for the combinations of all ages and approximate lens powers, but with attention being given to the fact that the starting optical eyeball model has generally common eye characteristics for the same age and approximate lens power, such an optical eyeball model is pre-constructed, which has a median value in each age class represented on the vertical axis and a median value in each approximate lens power class represented on the horizontal axis. The vertical axis representing M classes and the horizontal axis representing N classes allow for constructing M by N starting optical eyeball models. That is, employed is a table in which the vertical axis represents the age class (e.g., at five year intervals up to twenty years of age, and at 6 or 10 year intervals for 20 years of age or more) and the horizontal axis represents the approximate lens power (e.g., at intervals of 1.0 D). With this table, such a starting optical eyeball model is pre-constructed at a combination of median values in each class (e.g., the 35 years of age and the lens power of the amount of correction required being −2.5 D). Now, some values of the optical dimensions from the starting eyeball model constructed according to this embodiment are shown as an example.

Table 1 shows the values indicative of the depth of the anterior chamber applied from the correlation between the age and the approximate lens power.

TABLE 1

| AGE CLASS | Approximate lens power (D) | | | |
|---|---|---|---|---|
| | 0 | −2 | −4 | −6 |
| 18(10-26) | 3.58 | 3.75 | 3.87 | 3.98 |
| 36(27-44) | 3.42 | 3.57 | 3.70 | 3.80 |
| 47(45-49) | 3.10 | 3.25 | 3.37 | 3.44 |
| 55(50-59) | 2.94 | 3.10 | 3.23 | 3.31 |

Table 2 shows the values indicative of the length of the eye axis applied from the correlation between the age and the approximate lens power.

TABLE 2

| AGE CLASS | Approximate lens power (D) | | | |
|---|---|---|---|---|
| | 0 | −2 | −4 | −6 |
| 18(10-26) | 23.50 | 24.40 | 25.10 | 26.02 |
| 36(27-44) | 23.70 | 24.50 | 25.20 | 26.00 |
| 47(45-49) | 23.70 | 24.50 | 25.20 | 26.00 |
| 55(50-59) | 23.70 | 24.50 | 25.20 | 26.00 |

Since no significant change may appear in the shape of the eye at 60 years of age or more, this embodiment was designed to use the same values as those of the age class for 55 (50 to 59) years of age.

In accordance with the contents such as of the data from the aforementioned literatures, this embodiment also introduced the following parameters for each layer of the lens of the eye to be constructed by the optical eye model determining means. Now, an explanation is given below to the parameters introduced for the optical dimensions corresponding to the lens of the eye in the optical eyeball model.

The aspherical surface of the lens at each layer of the lens of the eye to be constructed by optical eyeball model constructing means is determined as expressed in the following equation.

$$Z = \frac{CY^2}{1 + \sqrt{1-(K+1)C^2Y^2}} + A_4 Y^4 + A_6 Y^6 + A_8 Y^8 + \ldots \quad \text{Equation 1}$$

In equation 1, R is the radius of the reference spherical surface, C is 1/R, and K is the eccentricity. Here, the aspherical surface coefficients $A_4$, $A_6$, $A_8$, . . . , are all set to zero because the first term sufficiently represents the shape of the lens.

Figure 4:
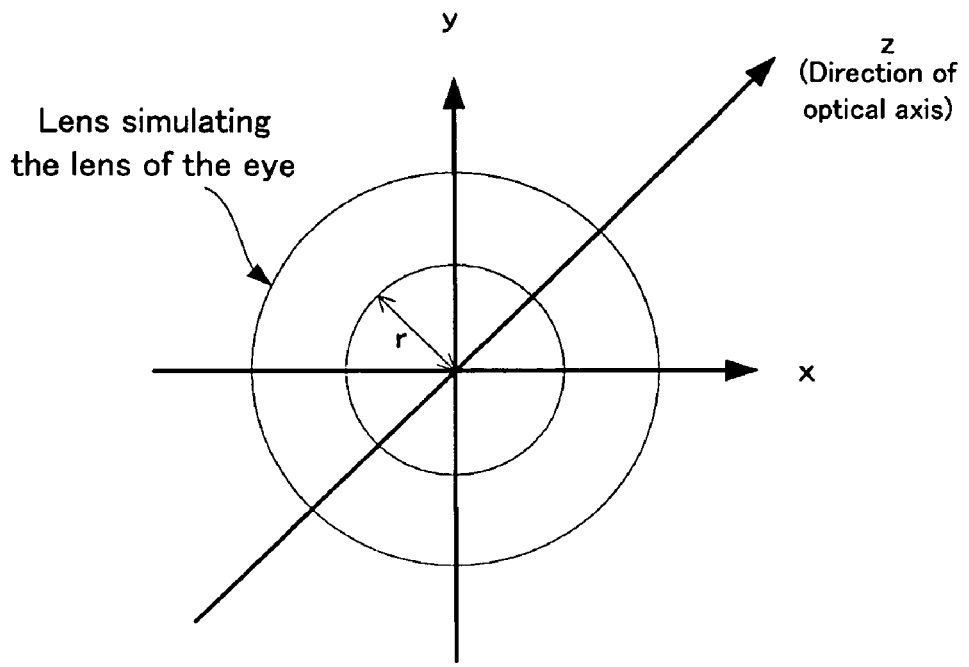
FIG. 4 is an explanatory pictorial view illustrating the refractive index distribution of each of lenses simulating the lens of the eye.

Furthermore, each lens simulating the lens of the eye is designed to have an uneven distribution of refractive indices exhibiting different refractive indices depending on the portion. As shown in FIG. 4, the following equation represents the refractive index nr that is apart by distance r from the lens center of each lens in a direction perpendicular to the optical axis:

$$n_r = n_{r0} - \delta n(r) \qquad \text{Equation 2}$$

In equation 2, $n_0$ is the refractive index at the lens center and $\delta n(r)$ is the amount of refractive index decreased with the distance from the lens center, $\delta n(r)$ being expressed by the following equation:

$$\delta n(r) = r^2/K_s \qquad \text{Equation 3}$$

In equation 3, $K_s$ is the refractive index distribution coefficient, and its value represents the degree of unevenness in the refractive index distribution of the lens. The value of the coefficient is determined for each lens in accordance with the data or the like of the aforementioned literatures. As shown in Table 3, with attention being given to the fact that the central portion of the lens of the eye has higher refractive indices, the lenses closer to the central portion in the direction of the optical axis of the plurality of lenses simulating the lens of the eye were designed to have higher values.

TABLE 3

| Lens | Refractive index distribution coefficient |
|---|---|
| R5-R6 | 250 |
| R8-R9 | 290 |
| R11-R12 | 325 |
| R13-R14 | 360 |
| R17-R18 | 400 |
| R19-R20 | 360 |
| R22-R23 | 300 |

As described above, for example, when the lens with a refractive index distribution coefficient $K_s$ of 200 has a refractive index $n_{r0}$ of 1.410 at the lens center, the refractive index of a portion apart by 1.0 mm from the lens center is 1.405 and that of a portion apart by 1.5 mm therefrom is 1.399.

Furthermore, as the eye to be strained or relaxed to thereby accommodate the refractive power, the optical eyeball model constructing means calculates optical dimensions using the power distribution coefficient describing the distribution of the accommodation power per unit length of each lens simulating the lens of the eye. Thus, the optical eyeball model constructing means determines the optical dimensions to simulate the lens of the eye in its strained and relaxed conditions. In this embodiment, the refractive index distribution coefficient $K_s$, the aspherical surface coefficient K, and the radius of curvature R were to vary the optical dimensions of each lens using the power distribution coefficient. Now, this will be explained below with reference to an example.

It is to be understood that accommodation can be performed from an accommodation midpoint to a −aD side (a near point distance) or to a +aD side (a far point distance) when the optical dimensions of the optical eyeball model have been determined at the accommodation midpoint. As used herein, D is the diopter the value of which is expressed by the reciprocal of the distance (measured in meters) from a reference point of the lens to the focal point. When accommodation is performed by bD to the relaxed side, the lens dimensions of the lens of the eye of the optical eyeball model are determined using the power distribution coefficient to multiply the values of the refractive index distribution coefficient $K_s$, the aspherical surface coefficient K, and the radius of curvature R at the accommodation midpoint by (1+xb/a), thereby determining an optical eyeball model that simulates the eyeball in its relaxed condition. Conversely, for accommodation being performed by bD to the strained side, the values of the optical dimensions at the accommodation midpoint are multiplied by (1−xb/a), thereby determining an optical eyeball model that simulates the eyeball in its strained condition. As described above, the starting optical eyeball model employs an optical eyeball model which represents any degree of relaxing or strain by varying the aforementioned optical dimensions of the lens of the eye depending on the accommodation power.

By way of example, the lens power at the accommodation midpoint is −5.02 D when the lens power of the subject is −10.2 D at the near point distance and −0.2 D at the far point distance. In this example, suppose that the refractive index distribution coefficient $K_s$ of each lens at the accommodation midpoint takes the value indicated at the second column from the left in Table 4. In this case, the refractive index distribution coefficients $K_s$ on the strained and relaxed sides take on the values shown in Table 4 from the values of of each lens and the amount of accommodation.

TABLE 4

| Lens | Accommodation midpoint refractive index distribution coefficient $K_s$ | α | Relaxed-side refractive index distribution coefficient $K_s$ | Strained-side refractive index distribution coefficient $K_s$ |
|---|---|---|---|---|
| R5-R6 | 250 | 0.400 | 350.0 | 150.0 |
| R8-R9 | 290 | 0.388 | 402.5 | 177.5 |
| R11-R12 | 325 | 0.385 | 450.0 | 200.0 |
| R13-R14 | 360 | 0.382 | 497.5 | 222.5 |
| R17-R18 | 400 | 0.375 | 550.0 | 250.0 |
| R19-R20 | 360 | 0.360 | 489.6 | 230.4 |
| R22-R23 | 300 | 0.333 | 399.9 | 200.1 |

On the other hand, the aspherical surface coefficient K takes on the values shown in Table 5.

TABLE 5

| Boundary surface No. | Accommodation midpoint aspherical surface coefficient K | α | Relaxed-side aspherical surface coefficient K | Strained-side aspherical surface coefficient K |
|---|---|---|---|---|
| R5 | 2.000 | 0.700 | 3.400 | 0.600 |
| R8 | −0.600 | 0.700 | −1.020 | −0.180 |
| R11 | −0.800 | 0.700 | −1.360 | −0.240 |
| R13 | −1.000 | 0.700 | −1.700 | −0.300 |
| R17 | −1.200 | 0.700 | −2.040 | −0.360 |
| R19 | −1.100 | 0.700 | −1.870 | −0.330 |
| R22 | −1.000 | 0.700 | −1.700 | −0.300 |
| R25 | −0.200 | 0.700 | −0.340 | −0.060 |

The reference spherical surface radius R takes on the values shown in Table 6.

TABLE 6

| Boundary surface No. | Accommodation midpoint reference spherical surface radius R | α | Relaxed-side reference spherical surface radius R | Strained-side reference spherical surface radius R |
|---|---|---|---|---|
| R5 | 7.122 | −0.295 | 10.102 | 5.500 |
| R8 | 5.308 | −0.299 | 7.572 | 4.086 |
| R11 | 4.230 | −0.301 | 6.052 | 3.251 |
| R13 | 3.622 | −0.341 | 5.496 | 2.701 |
| R17 | −3.346 | −0.240 | −4.400 | −2.699 |
| R19 | −3.833 | −0.183 | −4.692 | −3.240 |
| R22 | −4.634 | −0.144 | −5.414 | −4.051 |
| R25 | −5.858 | −0.085 | −6.402 | −5.399 |

In this embodiment, the power distribution coefficient has been determined in accordance with the values of living body measurement data on Japanese people and data from the literatures.

The model validity verifying means 206 verifies the validity of the optical eyeball model at the midpoint and at the accommodation limits on the near point and the far point sides.

The optical eyeball dimension accommodation range defining means 208 is designed to define the range of eyeball accommodation at the accommodation midpoint and display the image of an optical eyeball model that defines the range of eyeball accommodation at the accommodation midpoint.

On the other hand, the optical eyeball model focal power verifying means 212 verifies the focal power of the optical eyeball models at the three distances determined according to usage. For example, the three distances defined according to usage include 0.3 mm (a near distance) assuming reading or desk work, 0.5 to 0.6 m (intermediate distance) assuming work at personal computers, and 5 m (far distance) assuming the driving of cars. On the other hand, the optical eyeball model focal power verifying means 212 has a function to verify by comparison the focal power of the optical eyeball model of an uncorrected eye.

The visual image generating means 214 generates visual images viewed by the subject before and/or after the correction by means of an eyeglass/contact lens.

The sharpness score generating means 216 derives the sharpness score of the viewing by the subject before and/or after the correction by means of an eyeglass/contact lens.

The user client 1 is a terminal for the user to utilize upon subscribing to a vision measurement, and for example, implemented by a personal computer.

The user client 1 is an input/output device serving as an interface for the user, and more specifically, implemented by input devices such as a keyboard and a mouse and output devices such as a display.

The user client 1 has access means such as a WWW browser serving as an interface for communicating various types of data with the WWW server 30 in the electronic service center 2. When the user client 1 is a personal computer, the WWW browser is implemented as a program stored in its memory.

Now, an explanation is given to the case where this system is implemented using a homepage or the like on a network such as the Internet (a wide area computer network).

First, the electronic service center 2 uses the WWW server 30 to set up a homepage on the Internet.

The user uses the access means such as a WWW browser in the user client 1 connected to the wide area computer network to access the user information management means 230 employing the homepage of the electronic service center 2 as an interface in order to request for an vision measurement.

The electronic service center 2 allows the user authentication means provided in the WWW server 30 to verify whether the user is an authorized registered member in accordance with the password of the user and/or the user authentication information of the user identifier (ID). Thereafter, the user information management means 230 in the electronic service center 2 writes the information, which has been transmitted to request for registration via the wide area computer network from the user, onto the user information database for management.

At this time, suppose that it has been found that the user utilizes the vision measurement system for the first time. In this case, a window for entering general attributes or the like is transmitted to the user client 1 to request for the entry of data such as general attributes such as the address, the name, the birthday, and the telephone number, the condition of the eyes (difficulty in viewing an object at hand), and requirements for the eyeglass. The user then inputs necessary items at the user client 1 to transmit the items to the electronic service center 2.

Furthermore, the user also registers his password and user member identifier (ID) or the like, and the user information management means 230 writes the information from user onto the user information database via the wide area computer network for management.

The structure of each database to be managed by the database management means 232 in the electronic service center 2 is as follows.

The user information database stores user information, as information for identifying users, including general attributes such as the user code, the user identifier (ID), the user password, the address, the name, the birthday, and the telephone number.

Such user information is data entered on the user information register window transmitted to the user client 1 by the user information management means 230, the data being provided with the user code.

It is not always necessary to register data for all the items.

The user information identifier (ID) and the password may be determined on the service center side in accordance with the user information acquired off-line or may be provided automatically upon the first access by the user.

The reference database for measuring vision stores data for each user such as the purpose of use, the near point distance, the far point distance, the age, the previous power, the sharpness of vision of both eyes with the previous power, the balance between the right and left eyes with the previous power, the years of use of the previous eyeglasses, the type of contact lenses (when used together), the desired corrected sharpness of vision, and any eye disease affecting the vision.

A vision measurement database stores data such as uncorrected vision, corrected vision, the distance between the pupils, the farsighted condition correction power, the nearsighted condition correction power, the date of measurement, and the power determiner.

A vision table database stores data indicative of the relationship between the power and the Landolt ring.

A nearsightedness information database manages data registered therewith including the degree of myopia, the relationship between the degree of nearsightedness and the vision, the type of nearsightedness (power), and the remedy.

The nearsightedness or myopia means an eye which allows parallel beams of light incident upon the eye to focus on a point in front of the retina without any accommodation of the eye (the far point being finite in front of the eye).

The degree of myopia is expressed with the reciprocal of the far point distance (e.g., as with 1/0.5=2 D for a far point distance of 50 cm).

The relationship between the degree of myopia and the vision is as shown in Table 7.

TABLE 7

| Uncorrected vision | Degree of myopia | Corrected vision |
|---|---|---|
| 0.8 | −0.5 | 1.2 |
| 0.5 | −1.0 | 1.2 |
| 0.3 | −1.5 | 1.2 |
| 0.2 | −2.0 | 1.2 |
| 0.1 | −3.0 | 1.2 |
| 0.07 | −5.0 | 1.2 |
| 0.06 | −6.0 | 0.9 |
| 0.05 | −7.0 | 0.7 |
| 0.04 | −8.0 | 0.6 |
| 0.03 | −9.0 | 0.5 |

The types of myopia (power) are as follows.

Low degree of myopia (−4 D), Moderate degree of myopia (−4 D to −7 D), High degree of myopia (−7 D to −10 D), Highest degree of myopia (−10 D or more)

As a remedy for myopia, appropriate concave lenses are worn.

A farsightedness information database manages data registered therewith including the degree of hyperopia, the type of farsightedness, and the remedy for farsightedness.

The farsightedness or hyperopia means an eye which allows parallel beams of light incident upon the eye to focus on a point behind the retina without any accommodation of the eye (the far point being finite behind the eye).

The types of hyperopia, as expressed with their power, are as follows.

Low degree of hyperopia (+4 D), moderate degree of hyperopia (+4 D to +7 D), and high degree of hyperopia (+7 D); as a remedy for hyperopia, appropriate convex lenses are worn.

An astigmatism information database manages data registered therewith including the degree of astigmatism, the type of astigmatism, and the remedy. Astigmatism is a condition in which parallel beams of light incident upon the eye do not focus on one point without any accommodation of the eye.

The types of astigmatism are as follows.

Regular astigmatism (symmetric unevenness on the refractive surface)

Irregular astigmatism (different degrees of inflection in the same light path preventing the focusing of light)

The remedies for astigmatism are as follows.

Single astigmatism (a cylindrical lens of an appropriate power being worn)

Compound astigmatism (a combination of a cylindrical lens and a spherical lens being worn)

Irregular astigmatism (contact lenses being worn)

Figure 5:
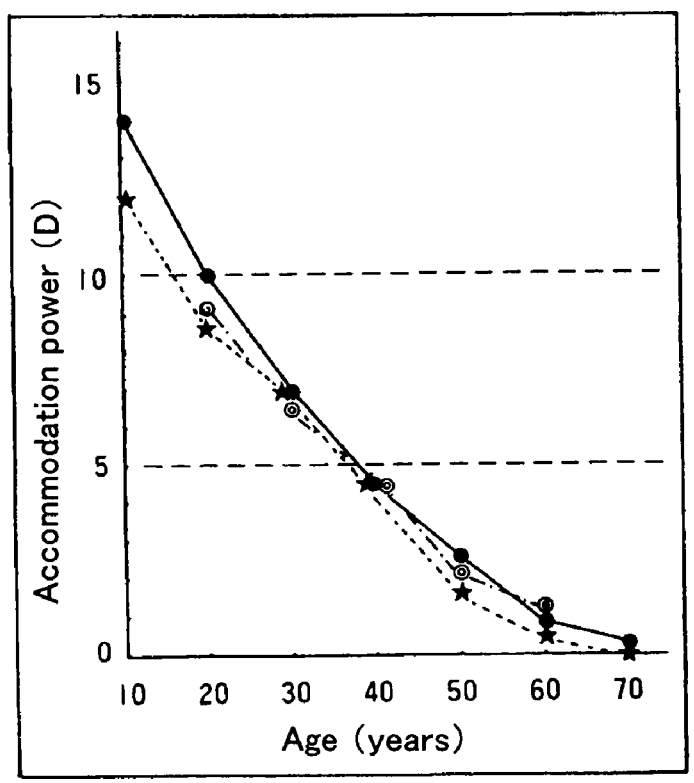
FIG. 5 is a view showing the relationship between the age and the accommodation power of the eye.

For example, as shown in FIG. 5, a database on the relationship between the age and the accommodation power of the eyeball manages an average accommodation power written thereon corresponding to each age.

A starting optical eyeball model database has an optical eyeball model pre-constructed therein which has a median value in each age class represented on the vertical axis and a median value in each approximate lens power class represented on the horizontal axis. Accordingly, with the vertical axis representing M classes and the horizontal axis representing N classes, recorded and managed are M by N starting optical eyeball models.

A visual image database writes thereon and manages the visual images and sharpness scores of the subject before and/or after the correction by means of an eyeglass/contact lens.

Now, an explanation is given below to a method for measuring vision using the remote subjective vision measurement system 10.

First, a method for measuring an uncorrected eye will be described.

Connecting the user client 1 to the electronic service center 2 causes an ID code input window to be sent as a user authentication window. The user authentication window prompts the user to input the user authentication information. The user client 1 receives and displays the user authentication window and then allows the user authentication information to be entered and sent to the electronic service center 2.

The user authentication information includes the password, the user ID, etc.

The electronic service center 2 receives the user authentication information, and in accordance therewith, the database management means 232 and the user information management means 230 retrieve the user information database for authentication.

The electronic service center 2 allows the database management means 232 to send a service menu window to the user client 1 as a member top page.

The user client 1 receives and displays the service menu window.

Then, on the service menu window, the user clicks the "uncorrected eye vision measurement" to measure the vision of an uncorrected eye.

This causes the wearing condition input window to be sent from the electronic service center 2 to the user client 1 via the WWW server 30. The wearing conditions include the purpose of wearing an eyeglass/contact lens (e.g., when the user wants to wear the eyeglass/contact lens, i.e., for viewing an object at hand, viewing an object at a distance, or driving a car) and a viewing environment (e.g., the range and distance of frequent viewing in daily life or the frequency of working at a personal computer).

Furthermore, the user information input window is sent from the electronic service center 2 via the WWW server 30.

As the information for identifying the user, the user information input window prompts the user to input user information including general attributes such as the user code, the user identifier (ID), the user password, the address, the name, the birthday, and the telephone number; and data concerning the purpose of use, the near point distance, the far point distance, the age, the previous power, the sharpness of vision of both eyes with the previous power, the balance between the right and left eyes with the previous power, the years of use of the previous eyeglasses, the type of contact lenses (when used together), the desired corrected sharpness of vision, and any eye disease affecting the vision.

Then, an uncorrected eye vision measurement window is sent from the electronic service center 2 to the user client 1 via the WWW server 30.

Figure 6:
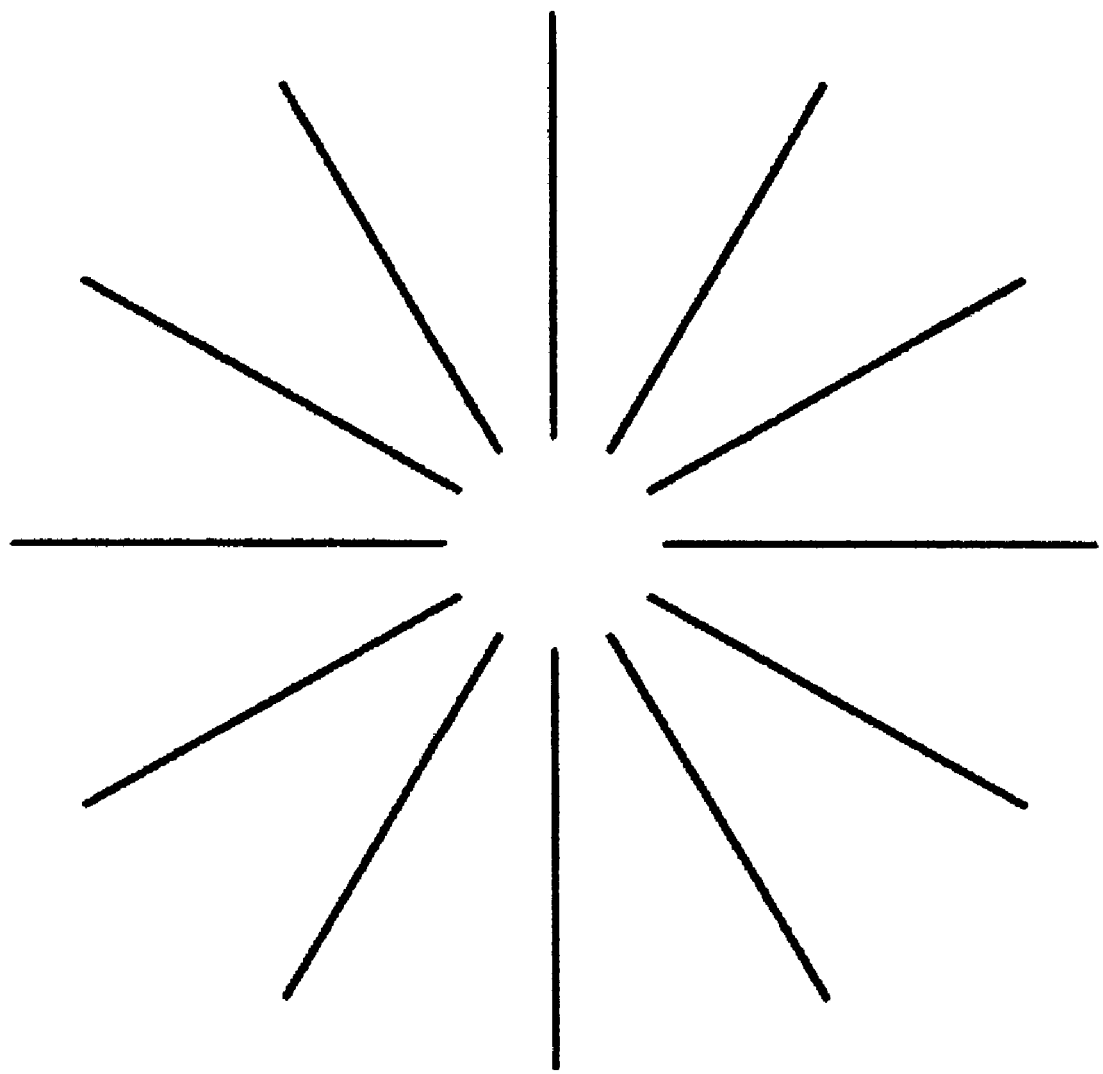
FIG. 6 is a pictorial view illustrating an example of an astigmatic axis determination chart.

First, the astigmatic axis determination chart shown in FIG. 6 is displayed, and the user checks any unevenness in viewing by varying the distance within a range of 1 m.

The user views the uncorrected eye vision measurement window (not shown) by one eye with the other eye being covered with a hand. The uncorrected eye vision measurement window shows an image or a viewed target to be gazed at with one eye.

Then, the user fixes his jaw to keep the distance constant from the uncorrected eye vision measurement window. For example, the user may put his jaw on the palms of his hands to fix his face with the elbows placed on the desk.

The near point distance is then measured. The near point distance measurement checks how close the subject can approach the screen viewing it with ease. The face is kept stationary where the subject can see the window without blurring, and then the distance between the screen and the eye is measured to provide the near point distance.

Thereafter, the far point distance is measured. The far point distance measurement checks how far the subject can go away from the screen viewing the screen with ease. The face is kept stationary at the most distant position where the subject can see the window without blurring (the position at which blurring starts to occur), and then the distance between the screen and the eye is measured to provide the far point distance.

A ruler or a yardstick is placed horizontally to measure the distance between the screen and the eye for input.

Figure 7:
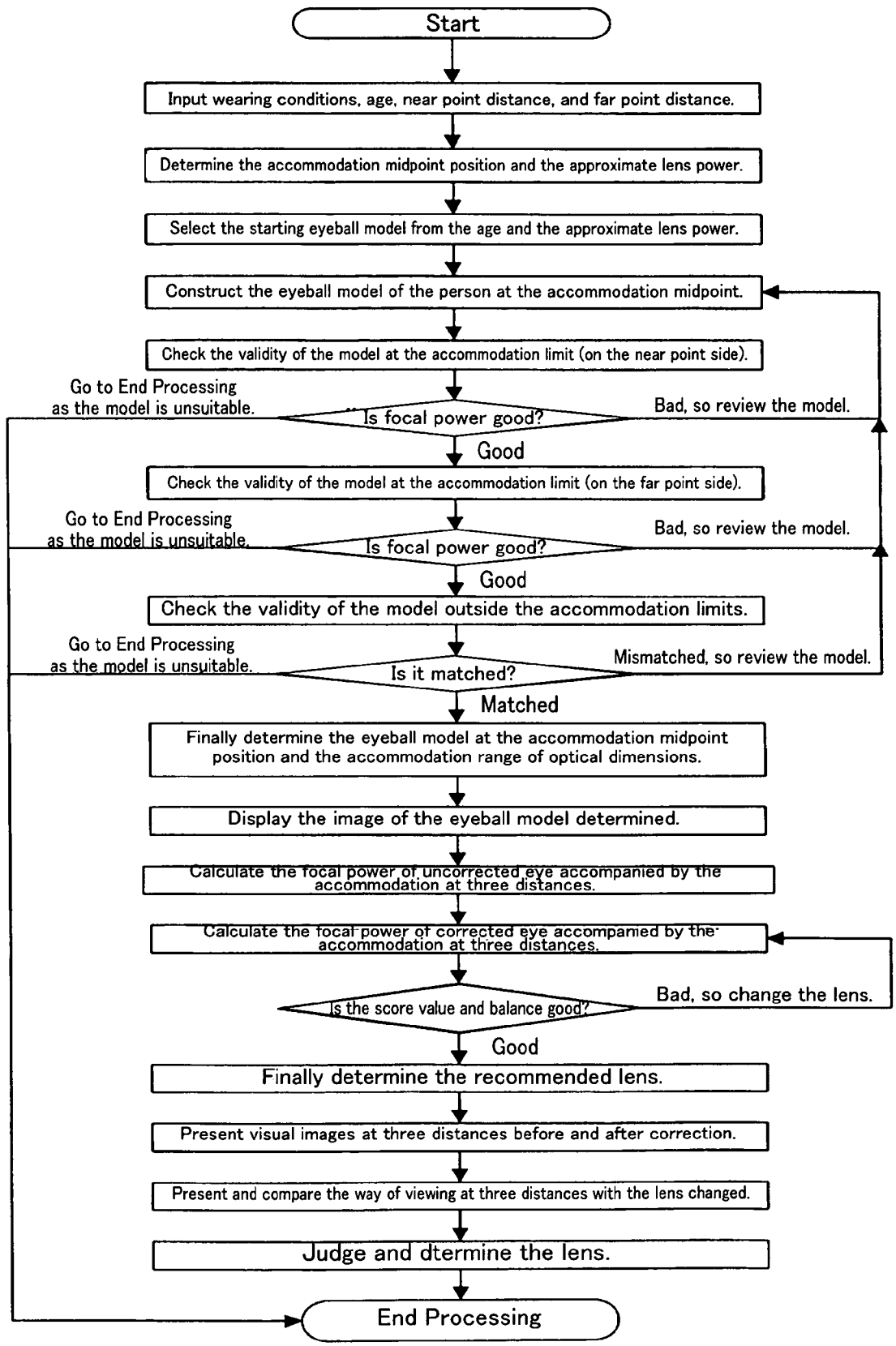
FIG. 7 is a view showing a processing flow of an eyeglass/contact lens power determination system.
Figure 8:
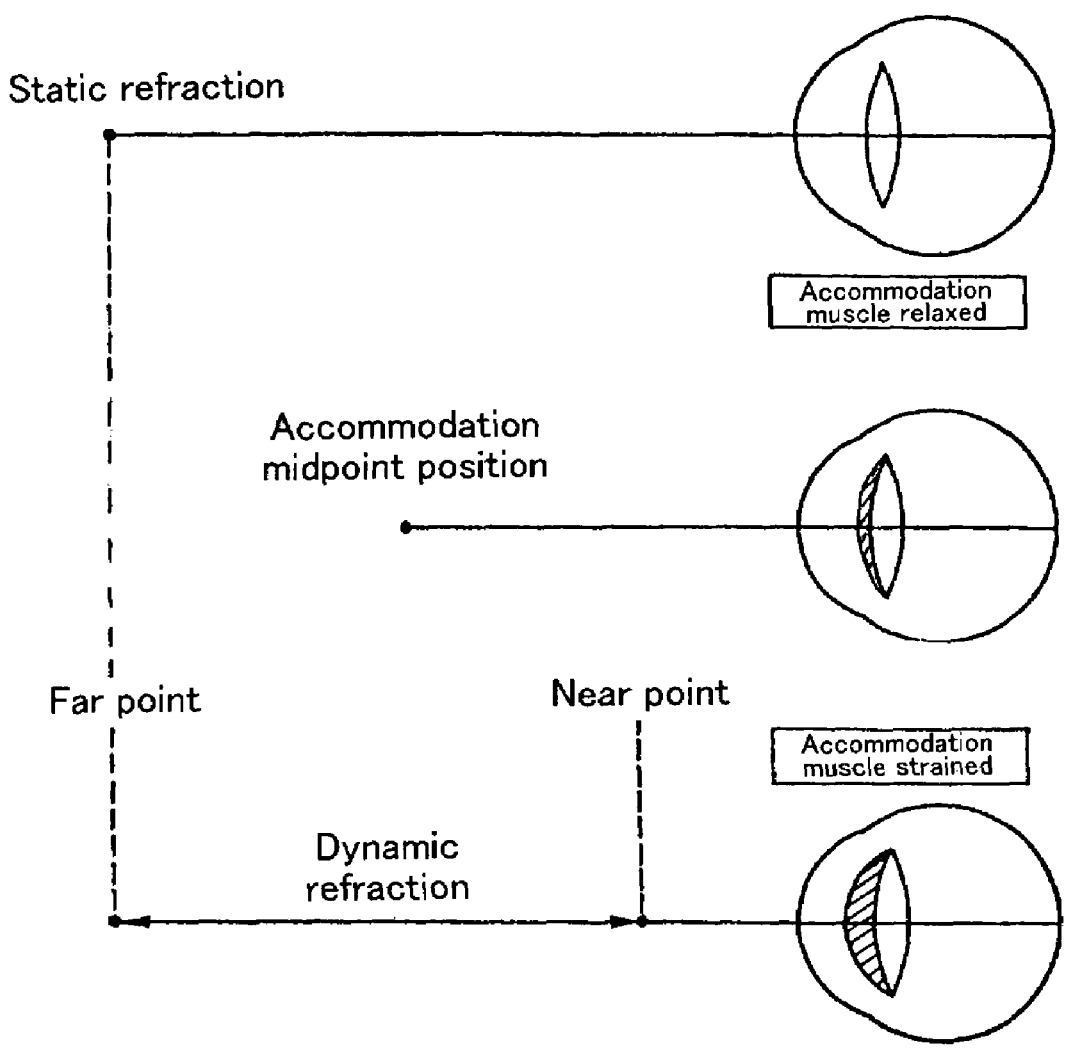
FIG. 8 is a schematic view illustrating a starting optical eyeball model.

Now, a method for determining the power of an eyeglass/contact lens will be described below with reference to the flowchart shown in FIG. 7.

First, as the information regarding the conditions of the eyes of the subject, the measured near point distance, the measured far point distance, the wearing conditions, and the age are entered at the inputting means 202 via the WWW browser. (The measured near point distance is provided by checking how close the subject can approach the screen viewing the screen with ease, in which the face is kept stationary where the subject can see the window without blurring, and then the distance between the screen and the eye is measured. The measured far point distance is provided by checking how far the subject can go away from the screen viewing the screen with ease, in which the face is kept stationary where the subject can see the window without blurring, and then the distance between the screen and the eye is measured. The wearing conditions include the purpose of wearing an eyeglass/contact lens, e.g., when the user wants to wear the eyeglass/contact lens, i.e., for viewing an object at hand, viewing a distant object, or driving a car, and a viewing environment, e.g., the range and distance of frequent viewing in daily life or the frequency of working at a personal computer).

The age relates to the accommodation power of the eye, in particular, to the elasticity of the lens of the eye, the accommodation power being decreased with advancing age (see FIG. 5). The accommodation power decreases with advancing age as mentioned above. This is conceivably because the elasticity of the lens of the eye is reduced with advancing age, thereby making it difficult to vary the refractive power in response to distance.

It is also estimated that the accommodation power becomes weaker with advancing age, but people at the same age have generally the same accommodation power.

For those who are nearsighted at their early ages, the measurement of the near point distance tends to yield an error. Thus, a correction table for correcting the error may be prepared in accordance with the results of a vision test separately carried out so as to correct the error in the near point distance.

Then, the approximate lens power of an eyeglass/contact lens is determined in accordance with the age and the information regarding the near point distance and the far point distance. The accommodation midpoint position is calculated from the approximate lens power derived from the far point distance and the near point distance. For example, assume that the far point distance is 1 m and the near point distance is 25 cm. In this case, the lens power required for the correction at the far point distance is −1.0 D (diopter), while the lens power required for the correction at the near point distance is −4.0 D (diopters). Considering that the approximate lens power lies at the center of them, it is given by (−1−4)/2=−2.5 D.

The distance at this time is the reciprocal of the approximate lens power, which gives 40 cm. The distance 40 cm is considered to be the accommodation midpoint position.

Then, the optical eyeball model determination means 204 determines a starting optical eyeball model from the age and the approximate lens power.

The starting optical eyeball model is an optical eyeball model pre-constructed which has a median value in each age class represented on the vertical axis and a median value in each approximate lens power class represented on the horizontal axis. With the vertical axis representing M classes and the horizontal axis representing N classes, M by N starting optical eyeball models will be present.

That is, for example, employed is a table in which the vertical axis represents the age class (e.g., at five year intervals up to twenty years of age, and at 10 year intervals for 20 years of age or more) and the vertical axis represents the approximate lens power (e.g., at intervals of 1.0 D). With this table, such a starting optical eyeball model is pre-constructed which takes the combination of median values in each class (e.g., the 35 years of age and the lens power of the amount of correction required being −2.5 D).

The entering of the specific age and the approximate lens power of the person allows for selecting one of the M by N starting optical eyeball models.

The starting optical eyeball model selected is employed as an initial value to perform automatic optical design processing for constructing an optical eyeball model unique to the person.

When compared with automatic optical design processing that employs a single starting optical eyeball model independent of the age and the approximate lens power, this starting optical eyeball model converges the automatic design processing more quickly at a higher speed of processing, making itself available on the Web. Furthermore, it provides more reliable solutions (the optical dimensions for the optimal focal power).

Now, a method for determining the starting optical eyeball model is described.

(1) One combination is assumed between the approximate lens power classes and the age classes. It is assumed that the intermediate state of human accommodation function is at the accommodation midpoint position, and the approximate lens power corrects the refractive power of the human eye in the intermediate state. The accommodation midpoint position is determined from the approximate lens power.

(2) Using this starting optical eyeball model, a beam of light is specifically entered to the eye from the accommodation midpoint position to evaluate the state of convergence of the light beam on the retina. To provide the optimal convergence, the automatic optical design processing is performed varying the optical dimensions to determine the optimal solutions (optical dimensions).

This is the same as the "human optical eyeball model construction processing at the accommodation midpoint", discussed later.

(3) Using a correlation table of average accommodation ranges corresponding to ages, and assuming an average accommodation range exists corresponding to an assumed age, the degrees of eyeball refraction are derived at the upper and lower limits of the accommodation range, based on which derived are the near point distance and the far point distance.

(4) The starting optical eyeball model is checked for validity at the accommodation limit (on the near point side) and at the accommodation limit (on the far point side). If valid, the model is determined as the starting optical eyeball model. If the light is badly converged, the process goes back to (3) to perform the processing again.

(5) The aforementioned processing is executed M by N times, thereby preparing M by N starting optical eyeball models.

(6) An overall consideration is made to the optical dimensions of the M by N optical eyeball models mainly in terms of contradiction and continuity, and then modifications are made thereto. In some cases, the processing will be repeated from (2). In particular, the processing is likely repeated to determine the refractive index distribution of the lens of the eye.

Then, an optical eyeball model of the subject is constructed at the accommodation midpoint.

In the construction of the optical eyeball model at the accommodation midpoint, the automatic optical design calculation begins with the aforementioned starting optical eyeball model to automatically determine the optical dimensions of a human eyeball so as to provide the optimal focal power.

As used herein, the automatic optical design calculation refers to the automatic process for determining optical dimensions by light beam tracking using an automatic lens design program. As a typical example of these techniques, the dumped least squares method is available, which is employed in this embodiment to perform the automatic aberration correction processing so as to provide the optimal focal power.

The automatic aberration correction processing provides a correction to satisfy a final performance condition (or a good focal power condition in which a plurality of beams of light are impinged from an infinitesimal point object located at the accommodation midpoint position upon the pupil diameter (e.g., $\phi=3$ mm) of the optical eyeball model at various heights of incidence to track the beams of light, thereby allowed to focus onto a point on the retina). Here, the correction is performed so as to minimize the sum of squares of the amount of deviation in position from the point of arrival of light on the retina while the optical dimensions are being gradually varied. In case the radius of curvature and the spacing between the surfaces of each lens were varied among the optical dimensions of the optical eye model for lenses having a spherical surface, and in case the radius of curvature of the reference spherical surface and the aspherical surface coefficient of the lenses were varied for lenses having an aspherical surface, it was found that the solutions were quickly converged. Thus, this embodiment was designed to perform the automatic aberration correction with the aforementioned optical dimensions employed as parameters in each of these cases.

Then, the model validity verifying means 206 is used to check the validity of the optical eyeball model at the accommodation limit (on the near point side).

In this validity check, the eyeball refractive power is brought up (UP) by the amount of accommodation power of a human eyeball, and then the automatic optical design calculation is performed to confirm a good focal power.

As used herein, the "bringing up (UP) the eyeball refractive power by the amount of accommodation power" means as follows.

Assuming that the far point distance is 1 m (−1.0 D) and the near point distance is 25 cm (−4.0 D), the accommodation midpoint position is 40 cm (−2.5 D) and an UP in the eyeball refractive power corresponding to the amount of correction of −1.5 D is required on the near point side with respect to the accommodation midpoint position.

As described above, an increase in eyeball refractive power corresponding to this −1.5 D is provided as follows. That is, the optical dimensions of the optical eyeball model are multiplied by (1+xb/a). Then, while the boundary conditions for the automatic optical design are being controlled, a plurality of beams of light are impinged from an infinitesimal point object located at a near point distance of 25 cm upon the pupil diameter (e.g., $\phi=3$ mm) of the optical eyeball model at various heights of incidence to track the beams of light. Thus, the automatic optical design is performed while the optical dimensions are being varied so as to focus the beams of light on a point on the retina.

Suppose that this has conceivably resulted in the convergence of the light on one point. In this case, it is determined that the optical model has been successfully simulated at the accommodation limit, and the optical eyeball model of the subject is valid at the accommodation midpoint.

Then, the model validity verifying means 206 checks the validity of the optical eyeball model at the accommodation limit (on the far point side).

In the validity check, the eyeball refractive power is brought down (DOWN) by the amount of accommodation power of a human eyeball, and then the automatic optical design calculation is performed to confirm a good focal power.

As used herein, the "bringing down (DOWN) the eyeball refractive power by the amount of accommodation power" means as follows.

Assuming that the far point distance is 1 m (−1.0 D) and the near point distance is 25 cm (−4.0 D), the accommodation midpoint position is 40 cm (−2.5 D) and a DOWN in the eyeball refractive power corresponding to the amount of correction of +1.5 D is required on the far point side with respect to the accommodation midpoint position.

As described above, a decrease in eyeball refractive power corresponding to this +1.5 D is provided as follows. That is, the optical dimensions of the optical eyeball model are multiplied by (1−xb/a). Then, while the boundary conditions for the automatic optical design are being controlled, a plurality of beams of light are impinged from an infinitesimal point object located at a far point distance of 1 m upon the pupil diameter (e.g., $\phi=3$ mm) of the optical eyeball model at various heights of incidence to track the beams of light. Thus, the automatic optical design is performed while the optical dimensions are being varied so as to focus the beams of light on a point on the retina.

Suppose that this has conceivably resulted in the convergence of the light on one point. In this case, it is determined that the optical model has been successfully simulated at the accommodation limit, and the optical eyeball model of the subject is valid at the accommodation midpoint.

Furthermore, the model validity verifying means 206 checks the validity of the optical eyeball model outside the accommodation limits on the near and far point sides, i.e., outside the range of accommodation of the eyeball.

Then, the optical eyeball dimension accommodation range defining means 208 finally determines the range of accommodation of the eyeball optical dimensions for the optical eyeball model at the accommodation midpoint position.

The optical eyeball model at the accommodation midpoint position and the range of accommodation of the optical dimensions are determined as follows.

The model validity verifying means 206 performs the processing for checking the validity of the optical eyeball model at the accommodation limit (on the near point side) and the model validity verifying means 206 performs the processing for checking the validity of the optical eyeball model at the accommodation limit (on the far point side). These checks determines, as a result of the processing for constructing an optical eyeball model of the person at the accommodation midpoint, that the optical eyeball model is valid at the accommodation midpoint position. The optical eyeball model is then used in the focal power calculation processing, discussed later, which is accompanied by accommodation at the three distances with the eye uncorrected, and the focal power calculation processing which is accompanied by accommodation at the three distances with the eye corrected.

It can be said that the range of changes in optical dimensions at the accommodation limits (in particular, the range of changes in thickness of the lens of the eye within which the lens of the eye is made thinner or thicker, in the radius of curvature of the front surface, and in the radius of curvature of the rear surface) has also been determined by the model validity verifying means 206 performing the processing for checking the validity of the optical eyeball model at the accommodation limit (on the near point side) and the model validity verifying means 206 performing the processing for checking the validity of the optical eyeball model at the accommodation limit (on the far point side).

The determination of them makes it possible to simulate the accommodation of the eye according to the distance to an object.

Then, the optical eyeball model image generating means 210 may also be used to display the image of the optical eyeball model determined, e.g., by producing an eyeball cross-sectional view and displaying the description of its optical eyeball model at the same time.

Then, the optical eyeball model focal power verifying means 212 is used to calculate and verify the focal power that is accompanied by the accommodation at the three distances with the eye of the subject being uncorrected.

In the calculation above, the amount of an increase (UP) or a decrease (DOWN) in eyeball refractive power from the accommodation midpoint position is determined according to the distance to an object to perform the automatic optical design while the boundary conditions are being controlled, like the model validity verifying means 206.

The optical dimensions determined as described above represent the condition of the eye in which the eyeball virtually performs focus accommodation.

The calculation is repeated until no more improvement can be made in focal power, and the resulting optical dimensions are determined as the best focal power at the distance to the object.

To evaluate the focal power, several hundreds of beams of light equally dispersed are impinged from an infinitesimal point object located at a certain distance upon the pupil diameter (e.g., φ=3 mm) of the optical eyeball model to track the beams of light, thereby calculating where the beams of light are focused on the retina. To evaluate the degree of blurring, the two-dimensional Fourier transform is performed on the intensity distribution of a point image on the retina, thereby calculating the spatial frequency characteristics (OTF) to evaluate the image.

For the three distances, any three distances are selected at which the way of viewing is significantly varied. For example, they are 0.3 m (near distance), 0.5 to 0.6 m (intermediate distance), and 5 m (far distance).

If the distance to the object is greater than to the far point, then the accommodation power at the far point distance is used to check the focal power.

If the distance to the object is less than to the near point, then the accommodation power at the near point distance is used to check the focal power.

If the distance to the object lies between the near point and the far point, then the eyeball refractive power is varied by the amount of accommodation power at the midpoint to check the focal power.

Then, the optical eyeball model focal power verifying means 212 is used to calculate and verify the focal power that is accompanied by the accommodation at the three distances after the correction with an eyeglass/contact lens.

That is, an actual eyeglass lens (with known radii of curvature of the front and rear surfaces of the lens and a known refractive index of the glass material) is placed in front of the optical eyeball model to perform a calculation like the focal power calculation processing with the eye uncorrected.

From the approximate lens power and the wearing conditions, an appropriate virtual lens is determined to perform an optical simulation on the focal power with the eyeglass/contact lens being worn.

On the other hand, when the balance between the sharpness scores at the three distances is badly kept, the lens power is slightly varied to perform the optical simulation again.

(A) Calculation of Sharpness Score

Now, the sharpness score generating means 216 is used to vary the optical dimensions of the eye within the range of accommodation to create the condition in which the focal power is optimally provided, calculating the sharpness score at that time.

Here, the focal power is evaluated, thereby calculating the sharpness score several hundreds of beams of light equally dispersed are impinged from an infinitesimal point object located at a certain distance upon the pupil diameter (e.g., φ=3 mm) of the optical eyeball model to track the beams of light, thereby calculating where the beams of light are focused on the retina. A value obtained by the two-dimensional Fourier transform being performed on the intensity distribution of the point image is called the spatial frequency characteristics (OTF). Checking how the intensity is distributed on the retina makes it possible to evaluate the degree of blurring. The spatial frequency is a value which represents the fineness of a stripe pattern and is defined as the number of stripes per unit length.

For a visual system, it is represented by the number of stripes per visual angle of 1 degree. For example, assuming that the spacing of the stripes is w (degrees), it is given that u=1/w (cycles/deg). The value of w used for the evaluation of blurring is found from the resolution of the retina, allowing the sharpness score to be calculated based on the value of u provided at that time.

Then, the lens power selecting means 218 is used to finally determine the lens to be recommended.

Figure 9:
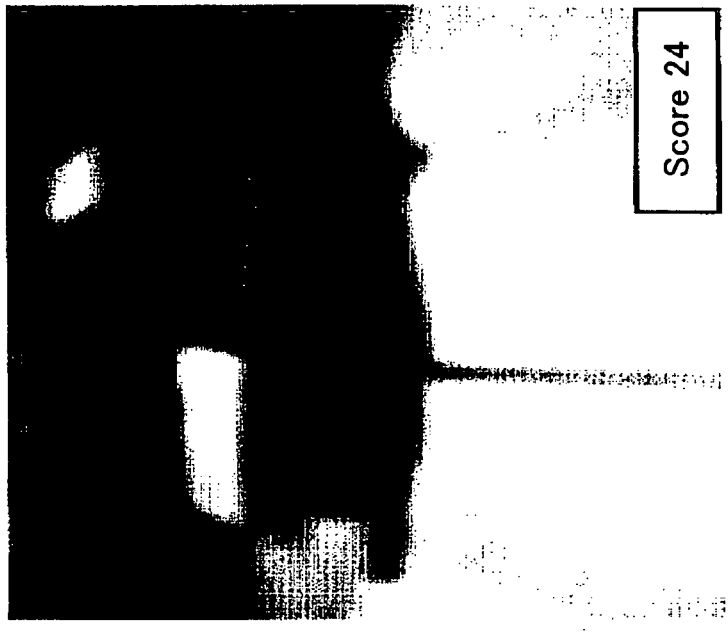
FIG. 9 is a pictorial view illustrating a method for representing an image presented.
Figure 9:
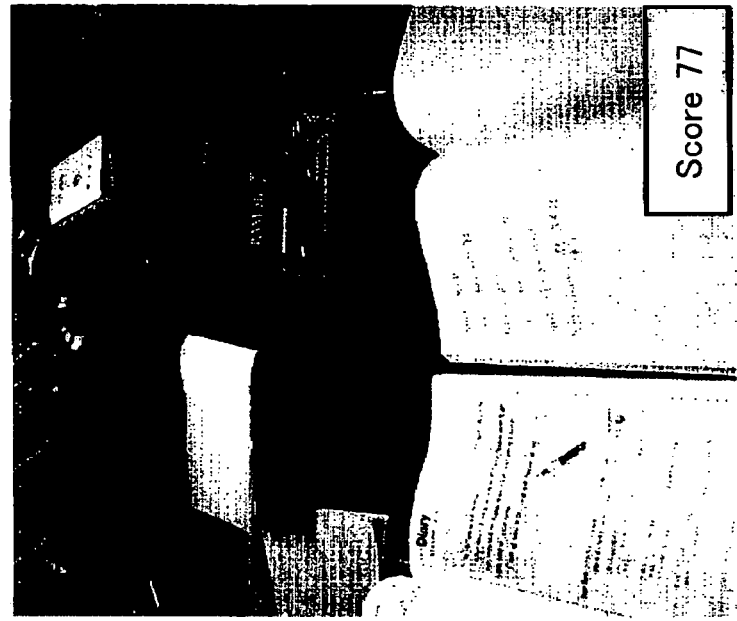
Figure 10:
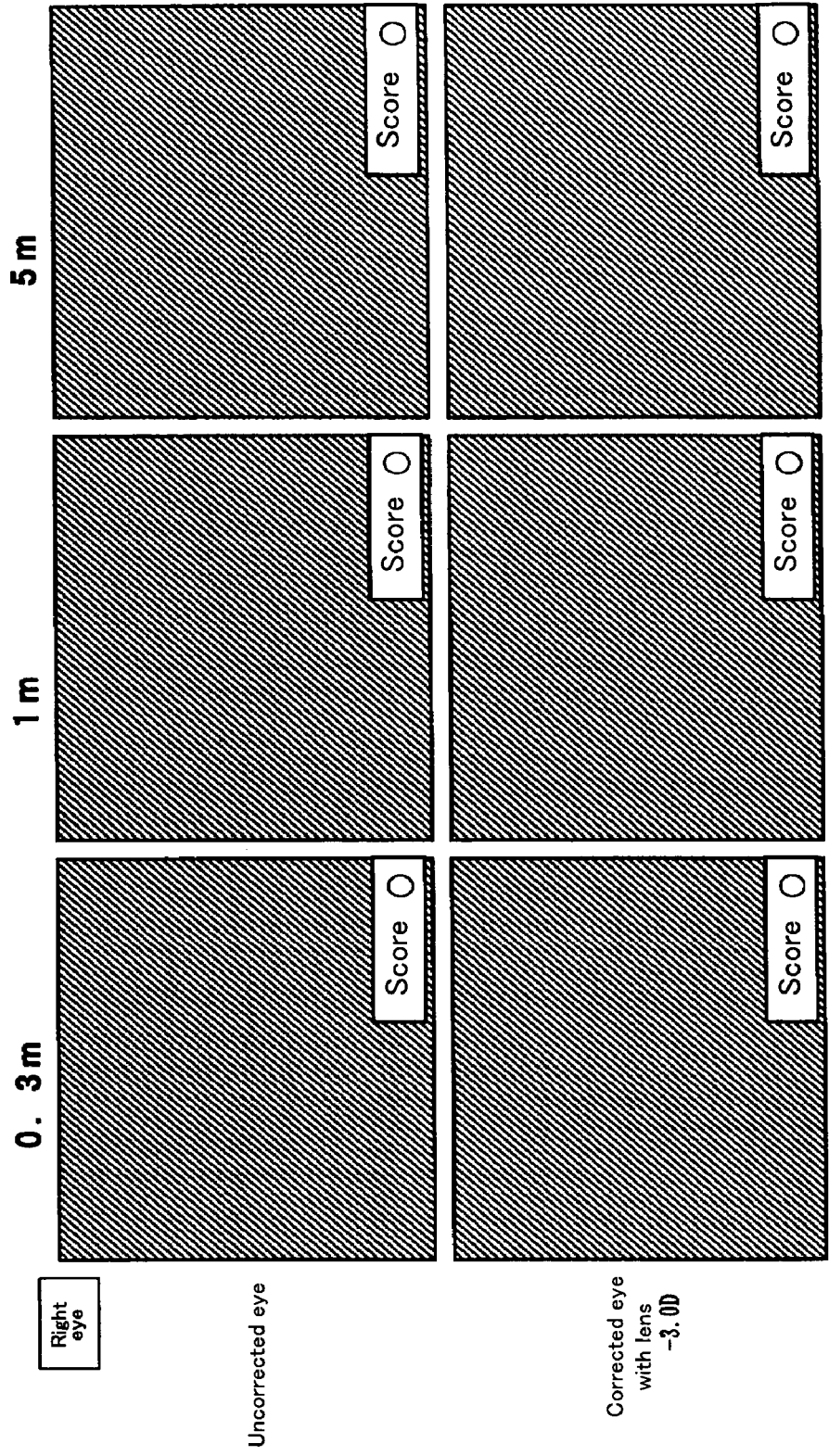
FIG. 10 show pictorial views illustrating images viewed before and after correction.

The visual image generating means 214 is then used to generate visual images at the three distances before and after the correction with the recommended lens. That is, the ways of viewing are presented for the uncorrected eye and for the recommended lens being worn. Furthermore, the aforementioned sharpness score is presented and displayed in the visual image (as shown in FIG. 9).

(B) Generation or Selection of Visual Image

The visual image generating means 214 is used to prepare images at the three distances which are photographed at high resolution.

The N by N size smoothing filter processing is performed on the images pixel by pixel to blur the images. The degree of blurring can be adjusted by the value of N (at a minimum of 3), filter weighting, and the number of times of the processing.

The spatial frequency analysis is performed on the images that have been filtered in order to determine the degree of blurring, which is in turn associated with the sharpness score that has been determined through the calculation of the sharpness score in (A) above.

Several images are prepared which correspond to some sharpness scores. Furthermore, the score values are calculated which correspond to the images obtained by the special smoothing filter processing being performed once on the prepared images.

The score value determined by the calculation of the sharpness score in (A) above is used to directly call the corresponding image for display or to filter the image to display the resulting image corresponding to its sharpness score.

Furthermore, the visual image generating means 214 is used to present viewed images at the three distances using a different lens for comparison. That is, using a different lens power, an optical simulation is performed with an eyeglass/contact lens being worn.

Then, the optical dimensions are varied within the range of accommodation of the eyeball to create the condition in which an optimal focal power is provided, thereby allowing the sharpness score at that time to be calculated.

On the other hand, if the sharpness score has been calculated at a particular lens power by means of the lens power selecting means 218, then that data is employed.

The electronic service center 2 allows outputting means 22 to send the viewed images produced as described above and the sharpness score to the user client 1 via the WWW server 30.

The electronic service center 2 also sends subjective vision measurement results separately prepared to the user client 1, allowing the result to be displayed on a subjective vision measurement result window. The subjective vision measurement results include the following items.

Included are DIST (indicative of a power for farsighted condition), READ (indicative of a power for nearsighted condition), SPH (indicative of a spherical power), CYL (indicative of an astigmatic power), AXIS (indicative of an axis), and P.D. (indicative of the distance between the center of the right eye and that of the left eye, i.e., the distance between the pupils).

Both the power for farsighted condition and the power for nearsighted condition are expressed for the right eye (R•) and the left eye (L•).

The current vision measurement with the automatic refractor is considered to provide the selection of a lens that optimizes the distant vision, in the case of which the lens is actually worn after the measurement to adjust the lens power to be selected taking the wearing conditions into account. However, this invention makes it possible to find the way of viewing at a plurality of distances with certain lenses being worn by means of the sharpness score. Thus, taking into account the wearing conditions which have been entered initially, the balance between the ways of viewing at the three distances can be considered to present the optimum lens power available with comfort. That is, although the subjective examination is currently essential by which the actual way of viewing is confirmed, it can be eliminated. This is preferably available for on-line shopping.

This embodiment has been designed to construct an optical eyeball model at the accommodation midpoint of the subject; however, without being limited thereto, it may also be designed to construct an optical eyeball model at a given point between the near point distance and the far point distance of the subject. In this case, the accommodation power can be distributed to the strained side or the relaxed side according to the accommodation position at which the optical eyeball model has been constructed, thereby constructing an optical eyeball model at the accommodation limit on the near point side or the far point side.

The aforementioned embodiment employed the starting optical eyeball models, each of which was pre-constructed based on the median value in each of M classes of age and N classes of approximate lens power, as the initial value used in the optical automatic design processing for constructing the optical eyeball model unique to a subject. However, without being limited thereto, such an optical eyeball model that is most suitable to the data entered by the subject may also be employed as the initial value for the optical automatic design processing. In this case, the amount of difference is added to or subtracted from the median value in a class in accordance with the age entered by the subject and the approximate lens power calculated, thereby allowing the optical eyeball model corresponding to the condition of the eyeball of the subject to be employed as the initial value. This makes it possible to perform the automatic aberration correction in less time than in the case where the automatic aberration correction is performed using the starting optical eyeball model that has been pre-constructed based on the median values.

Furthermore, this embodiment determined the value of w used for the evaluation of blurring from the resolution of the retina and allowed the sharpness score to be calculated from the value of u provided then; however, without being limited thereto, other techniques may also be employed to calculate the sharpness score. For example, the spatial frequency of an incident light beam is varied to find the value of a spatial frequency that provides an OTF value of 70%. In this case, the spatial frequency of the incident light beam is varied at equal intervals within a certain range to determine the spatial frequency which provides an OTF value of 70% with the minimum spatial frequency being zero and the maximum spatial frequency being 100, thereby providing the sharpness score that is developed from zero to 100.

This embodiment allows the visual image generated by the visual image generating means 216 to be viewed by the subject as it is; however, without being limited thereto, the degree of blurring of the image may be corrected and then the resulting image may be presented to the subject. This is because of the following reason. That is, human being tends to feel as if he/she clearly sees even an actually blurred visual image when he/she views an object or scenery which he/she has once viewed before or which is similar to it, because the visual information of human being is corrected according to the memory of the object or the scenery that he/she has seen once before. Therefore, more specifically, a number of subjects verify the difference between the image produced by the visual image generating means 216 and the degree of blurring that the subjects feel when actually viewing it. A correction coefficient table is prepared in accordance with the results of the verification to present the image to a subject based on the result obtained by correcting the degree of blurring according to the correction coefficient table.

On the other hand, this embodiment is designed such that the subject uses the uncorrected eye vision measurement window to actually measure how far the subject can stay away from the screen in order to input the data on the far point distance for calculating the approximate lens power; however, without being limited thereto, the far point vision may also be measured to calculate the far point distance.

Figure 11:
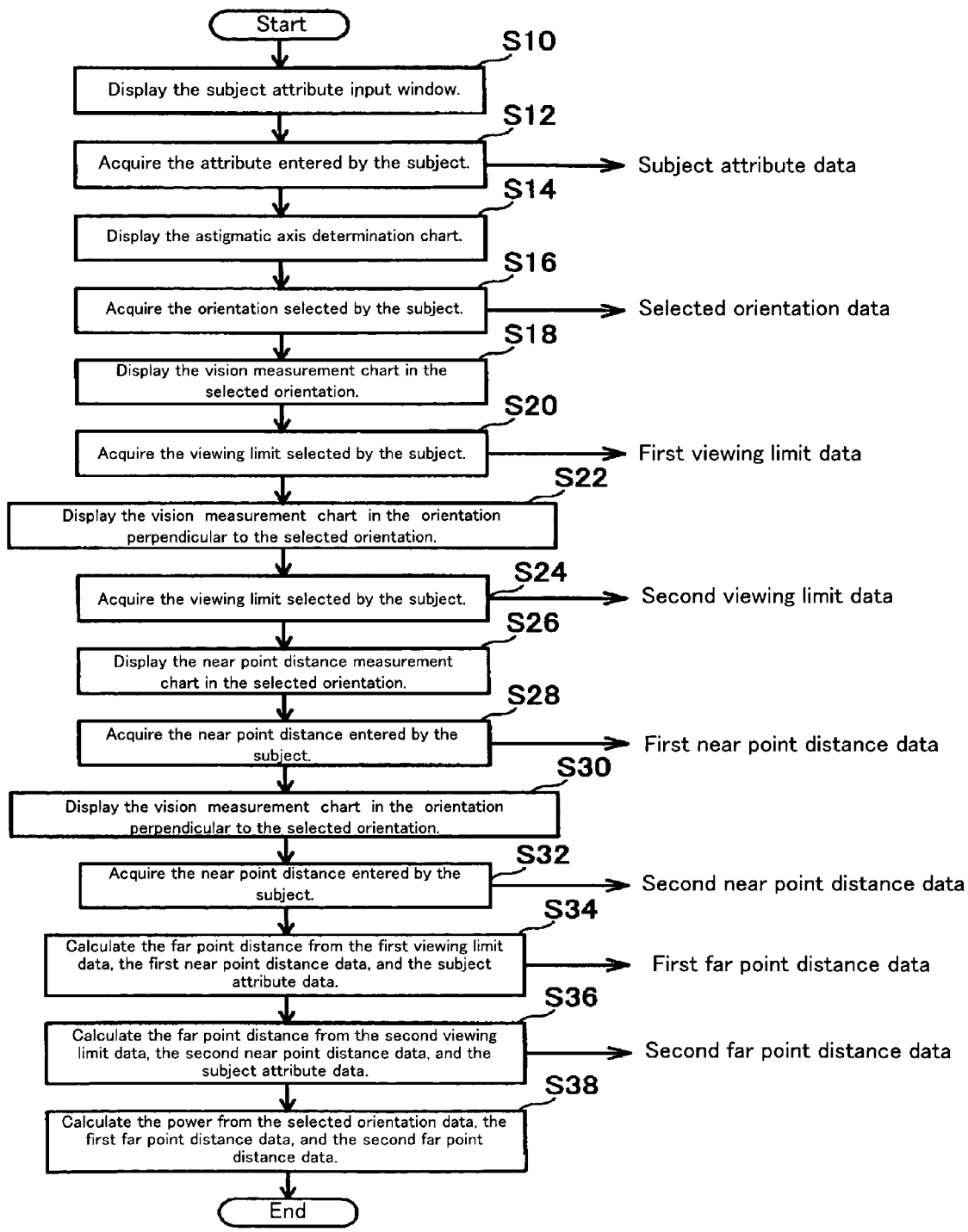
FIG. 11 is a view illustrating a processing flow of an optometer according to an embodiment of the present invention.
Figure 13:
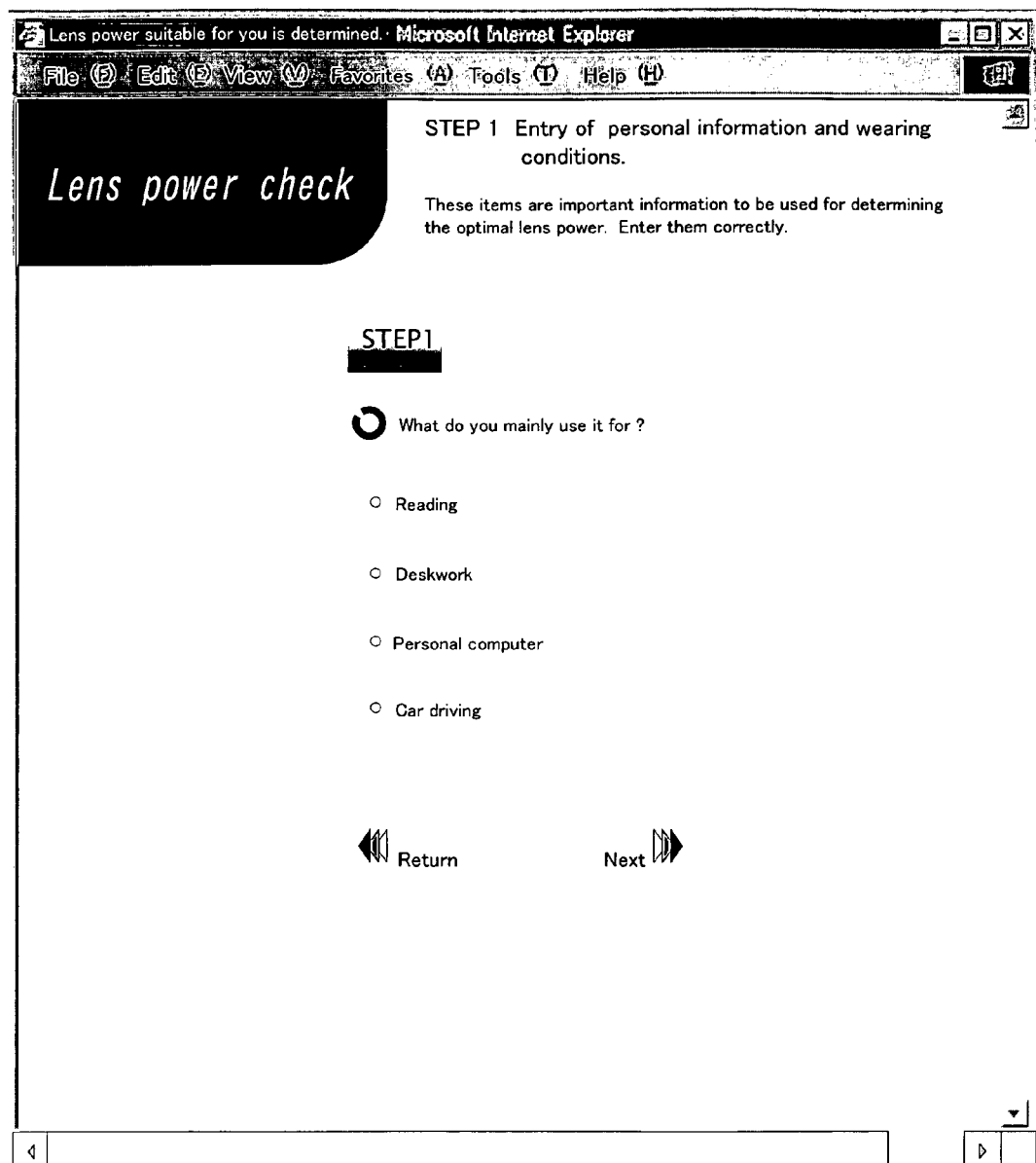
FIG. 13 is a view illustrating an example of a representation of a wearing condition input window.

FIG. 11 illustrates another embodiment which determines the astigmatic axis, measures the near point distances and measures the far point vision, including the processing for calculating the far point distance from the measured far point vision. First, the process displays a subject attribute input window for acquiring the attributes of a subject (S10), and then acquires the attributes entered by the subject to store them as the subject data (S12). The attributes of the subject include the personal information such as the age, the sex, and the height, and wearing condition information regarding the place where the eyeglasses or the contact lenses are mainly used. FIG. 12 is an example of a display window for acquiring personal information, FIG. 13 being an example of a display window for acquiring wearing conditions. Here, it is assumed that the "reading" and "deskwork" in the wearing conditions are for near distances, the "personal computer" for intermediate distances, and the "driving cars" for far distances.

Figure 14:
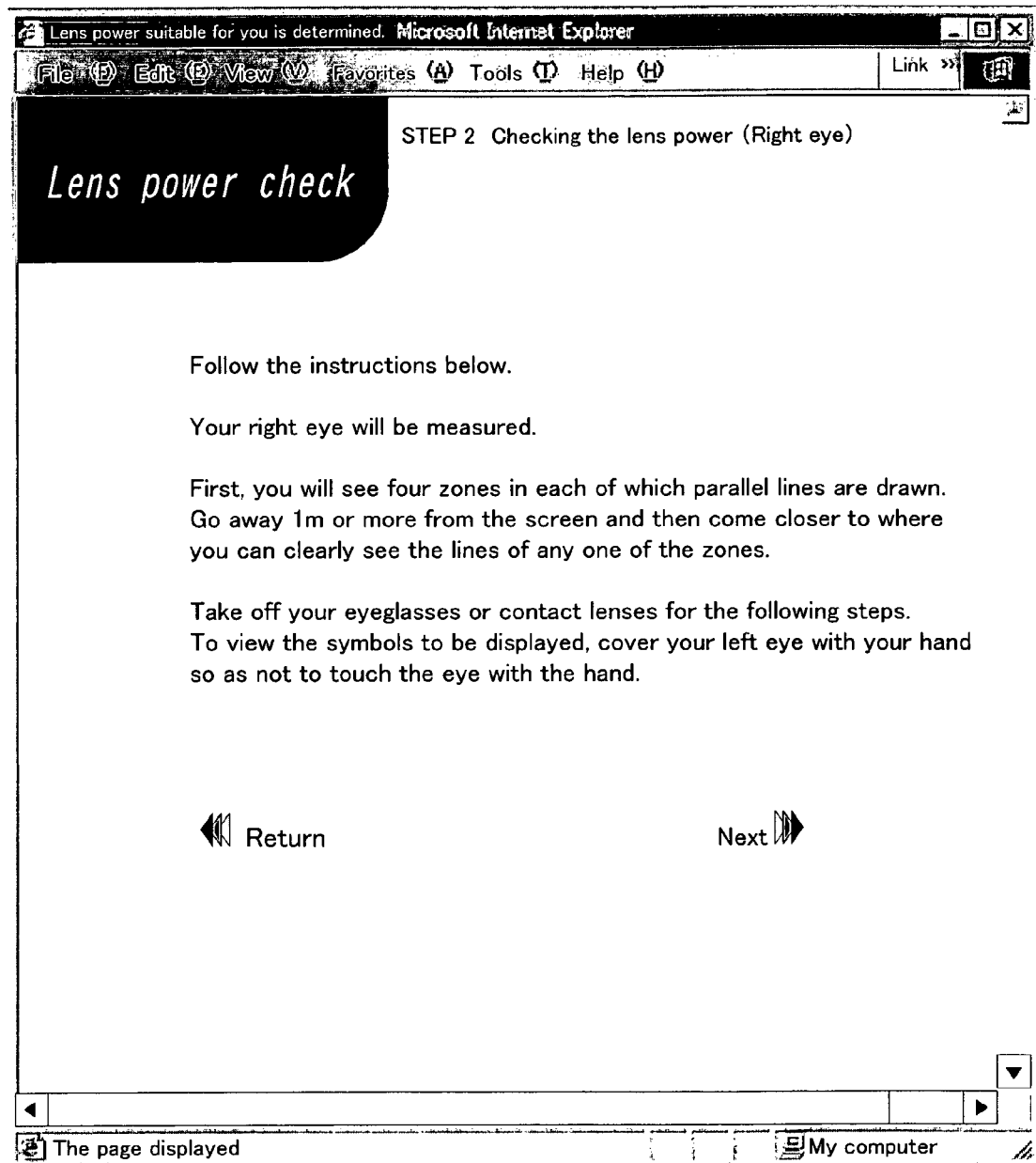
FIG. 14 is a view illustrating an example of a representation of an explanatory window for an astigmatic axis determination.
Figure 15:
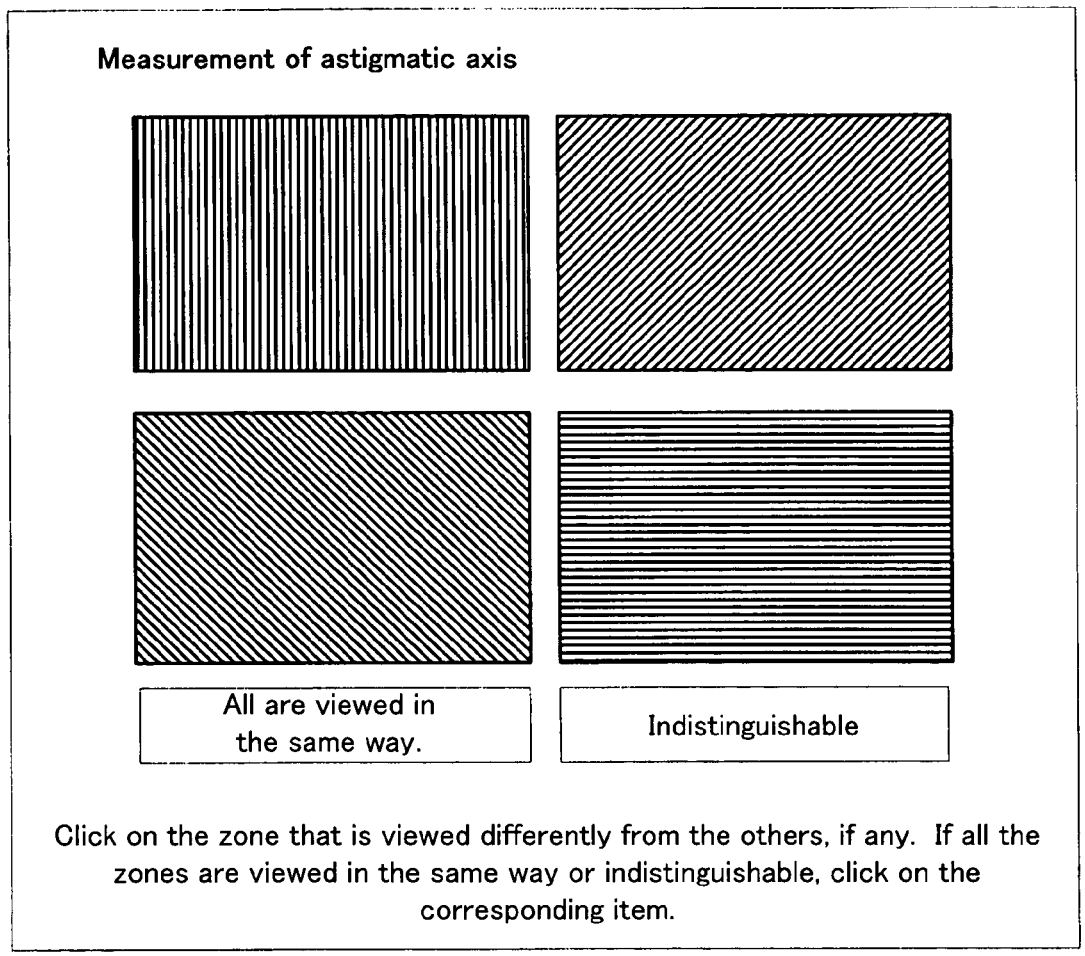
FIG. 15 is a view illustrating an example of a representation of an astigmatic axis determination window.

Then, the process displays an astigmatic axis determination chart for determining the astigmatic axis (S14) to acquire the orientation that the subject has selected and store it as selected orientation data (S16). FIG. 14 is an explanatory view illustrating an example of a window for use with the astigmatic axis determination, FIG. 15 showing an example of the astigmatic axis determination window.

As illustrated, the astigmatic axis determination chart is made up of four groups of a plurality of parallel lines, each group having lines extended in one orientation at an angle of 45 degrees, 90 degrees, 135 degrees, and 180 degrees, respectively. A subject with astigmatism experiences the orientation which provides the sharper viewing and the orientations which provide the less-sharper blurry viewing, and is prompted to click on the zone in the orientation that provides a different viewing. The process prompts the subject to select the orientation that provides a different viewing as mentioned above. This is because astigmatism may possibly cause a different orientation to provide the sharper viewing depending on the distance to the object, and thus employing the orientation that provides the sharper viewing at the first gaze would possibly cause an error in determination of the astigmatic axis. Therefore, the present invention is designed not to determine the main axis of the astigmatic axis at this stage but to make it clearly defined by determining the far point distance later.

In principle, a subject without astigmatism is probably provided with the same viewing in all the orientations. Thus, the subject who clicks on "All are viewed in the same way" or "Indistinguishable" is considered to have no astigmatism and undergoes the following measurements only in the horizontal orientation.

The astigmatic axis determination chart has the background in green and the lines in black, with the width of the lines having two pixels and the width between the lines having three pixels. A background color of white causes a miosis and a greater depth of field in the eyes due to its excessive brightness, thus raising a problem of providing reduced difference in the way of viewing the four zones. This is why the eye-friendly green base color is used to reduce brightness. A color of black was employed as the color of the lines because a number of subjects who underwent an eye examination experiment determined consequently that black could be viewed with ease. The width of the lines has at least two pixels because particularly in the case of a CRT display, one pixel may provide a different viewing between the horizontal/vertical and the diagonal direction due to the occurrence of focus blurring caused by the electron gun. The width between the lines was so set that the spacing between the lines could be recognized from a distance of 1 m because an extremely short distance to the chart in the astigmatism determination would vary the astigmatic axis, possibly resulting in an error in the determination. A vision of 1.0 (an angle of view of 0.1 degrees) indicates the capability of distinguishing a slit of 0.29 mm at a distance of 1 m, which generally corresponds to one pixel on a 14-inch liquid crystal display or a 17-inch CRT. Therefore, two pixels correspond to a vision of about 0.5. However, since those who take the eye test need eyeglasses, the spacing was further expanded to have three pixels.

On the other hand, the four orientations were provided for the astigmatic axis because of the following reasons. That is, this makes it possible to select sufficiently practical eyeglasses or contact lenses even using the four orientations, and the determination needs to be made as easily as possible without any error because the subject makes the determination by himself or herself.

Figure 16:
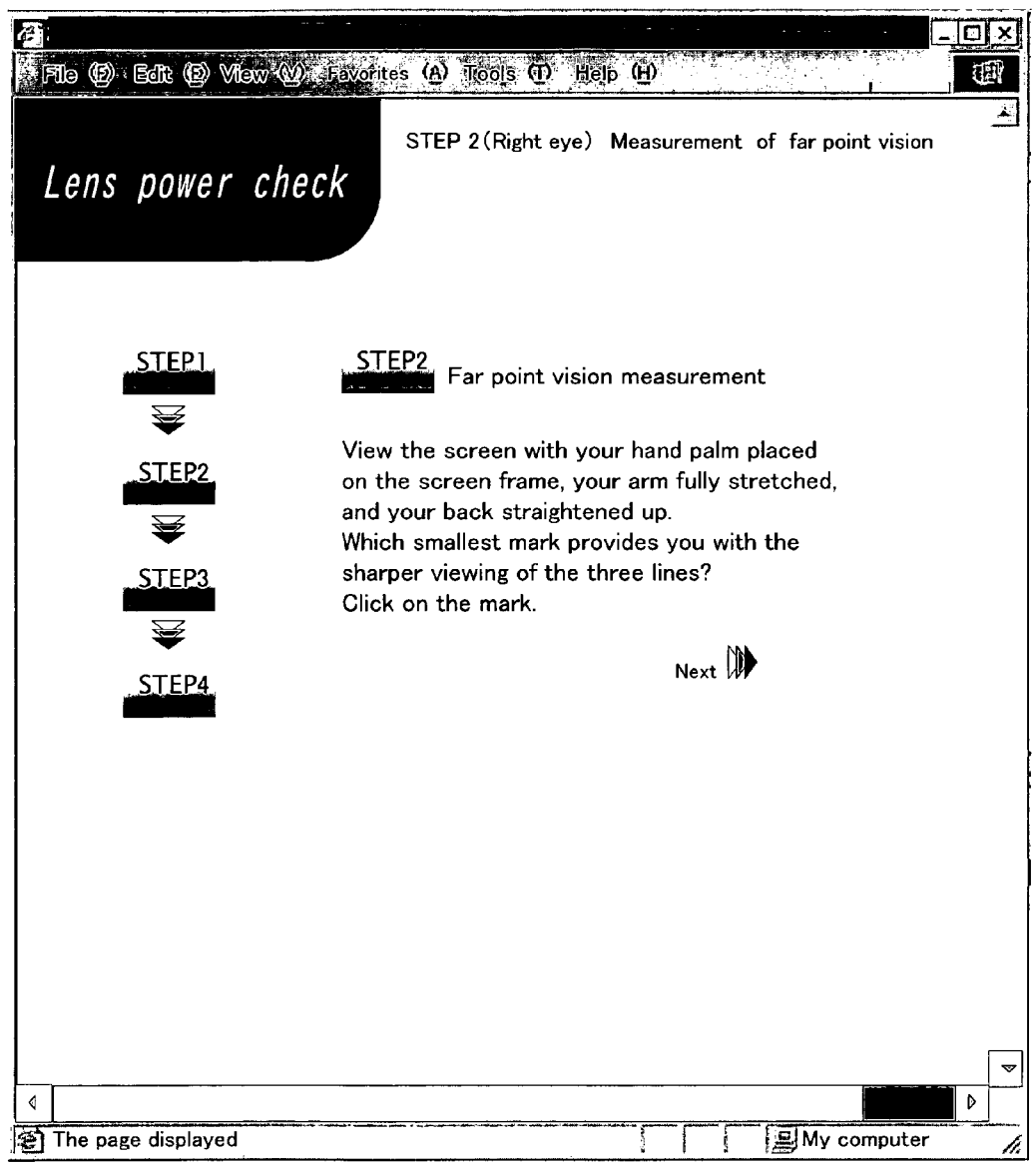
FIG. 16 is a view illustrating an example of a representation of an explanatory window for a far point vision measurement.
Figure 17:
FIG. 17 is a view illustrating an example of a representation of a far point vision measurement window.

Then, to measure the far point vision in the selected orientation that has been selected by the subject, the process displays the vision measurement chart for the selected orientation (S18) to acquire the viewing limit selected by the subject, which is then stored as first viewing limit data (S20). FIG. 16 is an explanatory view illustrating an example of a window for a far point vision measurement, FIG. 17 showing an example of the far point vision measurement window.

As illustrated, the vision measurement chart is a light and dark line image made up of three black lines and two white lines of a certain line width, a plurality of the charts being displayed in each of which the width of the lines are varied in I steps (from about 10 steps to 20 steps) corresponding to vision. On the vision measurement charts, the subject is prompted to click on the smallest mark that the subject can distinguish the three lines. Since the subject is allowed to select the mark that provides the viewing of three lines as described above, the subject can make a determination more easily when compared with the Landoldt ring that is viewed to visually distinguish a single gap.

The subject is urged to measure the far point vision at a reach from the computer screen. This is because the length of the arm is proportional in length to the height, and thus the distance between the subject and the chart can be predicted in accordance with the data on the height entered in advance.

As described above, the measurement can be conveniently carried out because the subject does not need to measure the distance to the computer screen or adjust the window display size.

Likewise, to measure the far point vision in the orientation perpendicular to the selected orientation selected by the subject, the process displays the vision measurement chart in the orientation perpendicular to the selected orientation (S22), and the viewing limit selected by the subject is acquired and stored as second viewing limit data (S24).

Figure 18:
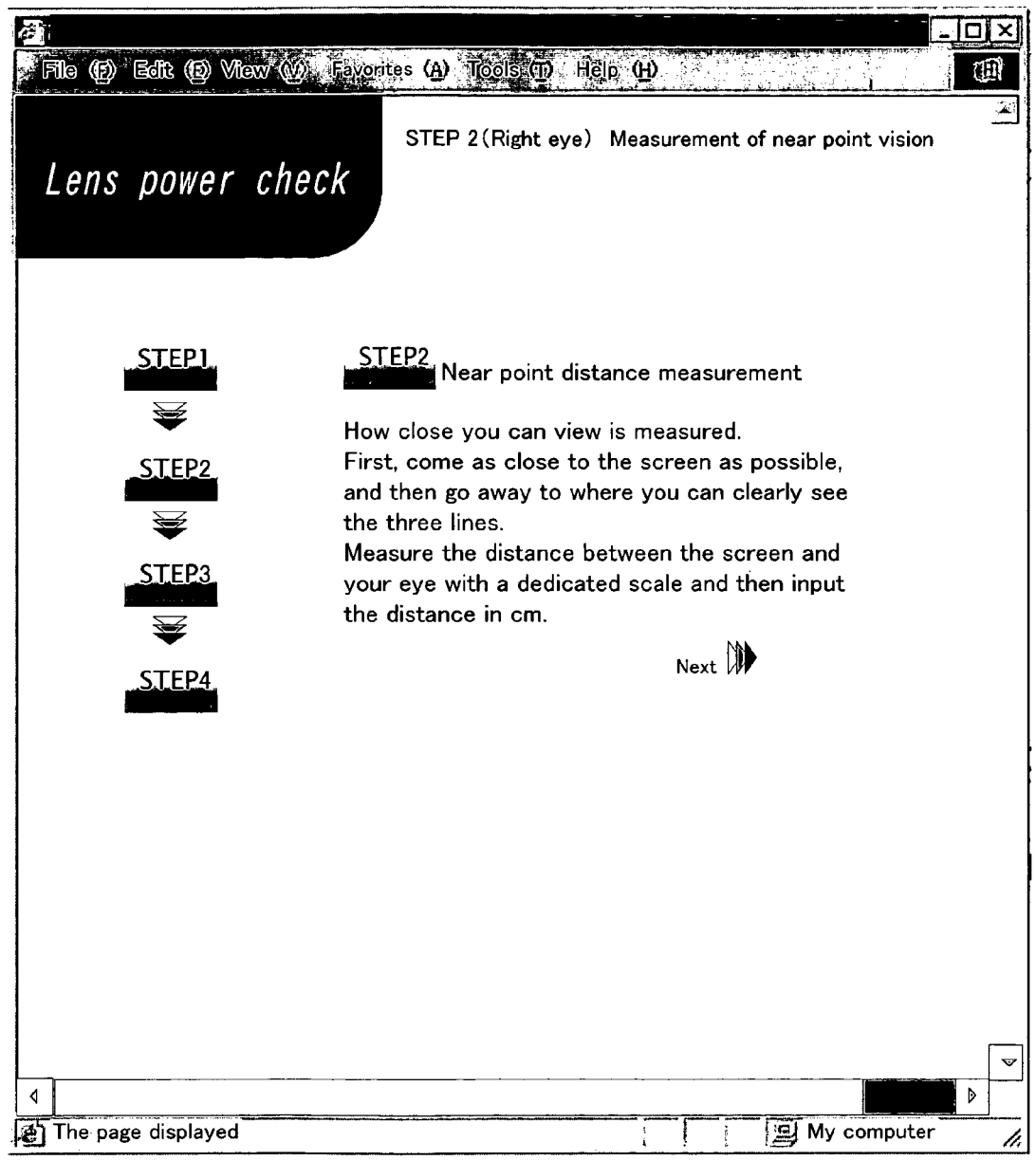
FIG. 18 is a view illustrating an example of a representation of an explanatory window for a near point distance measurement.
Figure 19:
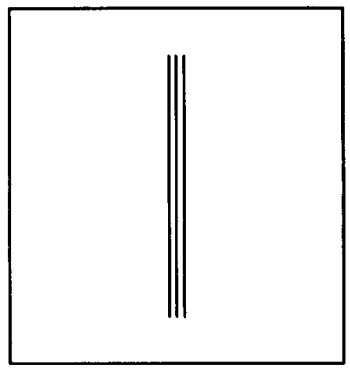
FIG. 19 is a view illustrating an example of a representation of a near point distance measurement window.

Then, to measure the near point distance in the orientation selected by the subject, the process displays a near point distance measurement chart in the selected orientation (S26) to store the near point distance entered by the subject as the first near point distance data (S28). FIG. 18 is an explanatory view illustrating an example of a window for a near point distance measurement, FIG. 19 showing an example of the near point measurement window.

As illustrated, the near point distance measurement chart has three black lines provided in a green background. The message on the screen urges first the subject to come as close to the screen as possible and then go away therefrom to a position at which the subject can clearly see the three lines and measures the distance between the eyes and the screen, thereafter prompting the subject to input the distance in centimeters.

The near point distance measurement chart employs thinner lines compared with the aforementioned vision measurement chart because the chart is viewed in close proximity to the computer screen. However, because of the difference in resolution due to the age, thin lines are used for the youth and slightly bolder lines are used for the middle aged and the elderly people.

To measure the near point distance in the orientation perpendicular to the selected orientation selected by the subject, the process displays a near point distance measurement chart in the selected orientation (S30) to store the near point distance entered by the subject as the second near point distance data (S32).

Then, the process determines the far point distance from the first viewing limit data, the first near point distance data, and the subject limit data to store the resulting distance as the first far point distance data (S34). Likewise, the process determines the far point distance from the second viewing limit data, the second near point distance data, and the subject limit data to store the resulting distance as the second far point distance data (S36).

Figure 20:
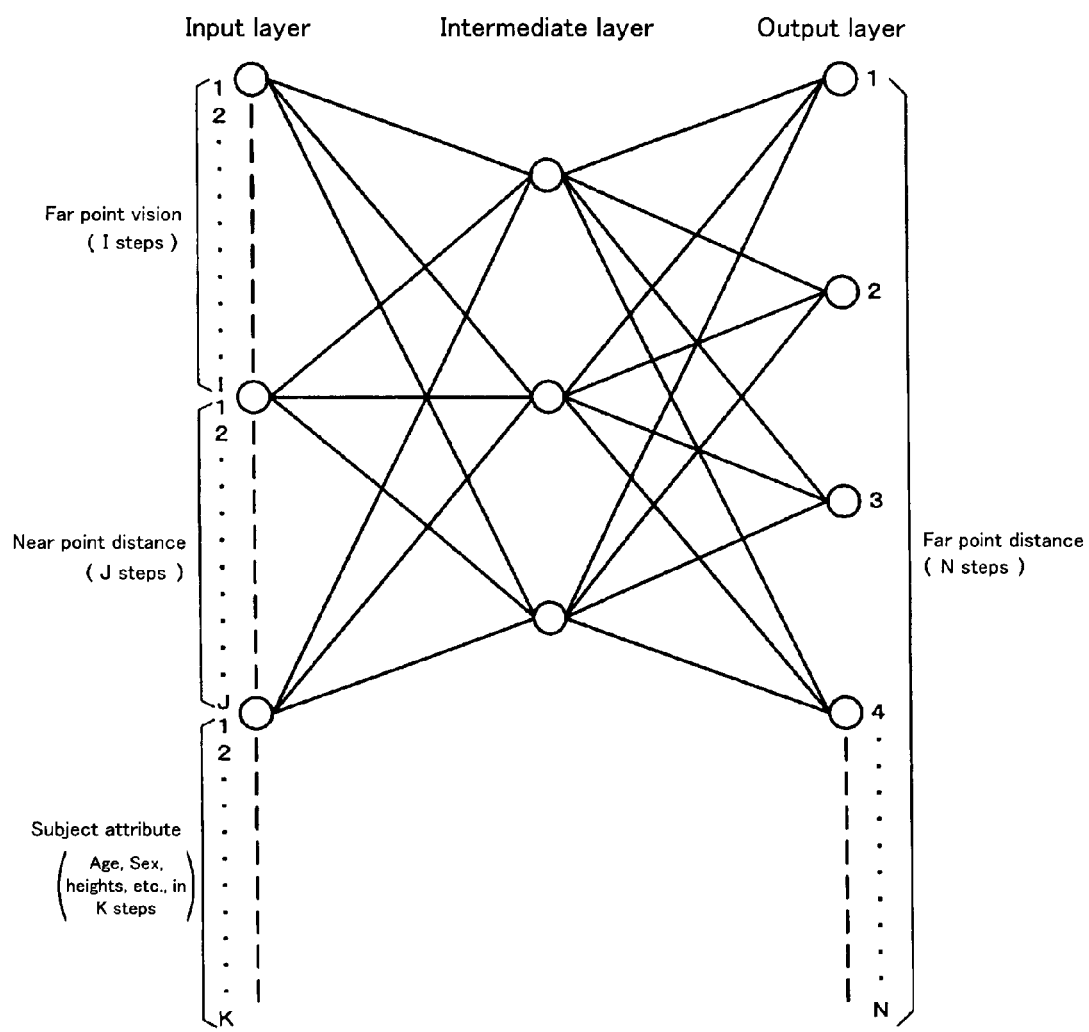
FIG. 20 is a view illustrating an example of a configuration of a neural network for calculating a far point distance.

The far point distance is operated using a neural network that a number of subjects have taught in advance. FIG. 20 is a view illustrating an exemplary configuration of a neural network for operating the far point distance. As illustrated, the input layer has I steps of far point vision (the viewing limit selected by the subject on the vision measurement chart), J steps of near point distance (the near point distance measured by the subject on the near point distance measurement chart), and K steps of subject attributes (the age, the sex, and the height), while the output layer has N steps of far point distance. The age and sex are employed as parameters because the accommodation power of the eyes of the subject is varied due to them. The height, as described above, that is proportional to the length of the arm is used as a substitute parameter in order to adjust the distance between the subject and the screen to the length of the arm. As the method of learning, employed is the so-called back-propagation method.

Here, to make the conversion into the lens power easier, the near point distance of the input parameters and the far point distance resulted from the operation are each converted for handling to the value D (diopter) or the reciprocal of the distance measured in meters.

The neural network was designed to produce two independent learning models in the selected orientation of the astigmatic axis and the orientation perpendicular to the selected orientation to perform calculations for each of them separately.

Since different types of displays provide different ways of viewing the screens, the operation was performed using neural networks that had been separately taught depending on the display being either the liquid crystal display or the CRT.

The aforementioned embodiments are designed to calculate the approximate lens power from the far point distance; however, without being limited thereto, the approximate lens power may also be determined from the far point vision entered. In this case, a corresponding table is used, which is prepared in accordance with statistical data and stores the approximate lens power corresponding to the value of the far point vision, to determine the approximate lens power based on the corresponding table.

Furthermore, in the process of determining the lens power, the aforementioned embodiments verify the focal power of the optical eyeball models at the three distances, i.e., the near distance (0.3 m), the intermediate distance (0.5 to 0.6 m), and the far distance (5 m); however, without being limited thereto, the focal power may also be verified at a distance other than those distances and may not always be verified for all of the near distance, the intermediate distance, and the far distance.

INDUSTRIAL APPLICABILITY

As described above, the present invention constructs the optical eyeball model unique to a subject, thus making it possible to determine the power of an eyeglass/contact lens that is suitable for an individual.

The invention claimed is:

1. A system for determining an eyeglass/contact lens power, the system comprising:
   inputting means for entering information on a condition of a subject's eye;
   means for determining an optical eyeball model corresponding to the information on the eye condition entered through said inputting means; and
   means for selecting a lens power for verifying a focal power of an eyeglass/contact lens worn by the subject using the optical eyeball model determined by said optical eyeball model determining means.

2. The system for determining an eyeglass/contact lens power according to claim 1, wherein said inputting means includes means for displaying an astigmatic axis measurement chart to measure an astigmatic axis.

3. The system for determining an eyeglass/contact lens power according to claim 1, wherein said inputting means includes means for displaying a far point vision measurement chart to measure far point vision.

4. The system for determining an eyeglass/contact lens power according to claim 3, wherein said inputting means has means for calculating a far point distance from the far point vision measured.

5. The system for determining an eyeglass/contact lens power according to claim 4, wherein said inputting means has means for determining an approximate lens power from said far point distance calculated.

6. The system for determining an eyeglass/contact lens power according to claim 1, wherein said inputting means includes means for displaying a near point distance measurement chart to measure a near point distance.

7. The system for determining an eyeglass/contact lens power according to claim 1, wherein said optical eyeball model simulates each layer of an anterior cortex, a nucleoplasm, and a posterior cortex of the lens of the eye using a combination of plurality of lenses, respectively.

8. The system for determining an eyeglass/contact lens power according to claim 7, wherein said optical eyeball model has a characteristic that a refractive index of each of said lenses simulating the lens of the eye is decreased with a distance from the center of the lens.

9. The system for determining an eyeglass/contact lens power according to claim 8, wherein said optical eyeball model has a refractive index distribution characteristic that the refractive index of each of said lenses simulating the lens of the eye is expressed by (a refractive index at the center of the lens)—((the square of a straight distance from the lens center)/(a refractive index distribution coefficient)).

10. The system for determining an eyeglass/contact lens power according to claim 7, wherein the refractive index distribution coefficient of each lens simulating the lens of the eye is decreased with the distance from the center of said plurality of lenses in a direction of the optical axis simulating the lens of the eye to the direction of the optical axis.

11. The system for determining an eyeglass/contact lens power according to claims 7, wherein said optical eyeball model calculates optical dimensions using a power distribution coefficient describing the distribution of accommodation power per unit length of each lens simulating the lens of the eye.

12. The system for determining an eyeglass/contact lens power according to claim 1, wherein said means for determining an optical eyeball model determines a starting optical eyeball model in accordance with an age of the subject and information on the eye such as an approximate lens power.

13. The system for determining an eyeglass/contact lens power according to claim 1, wherein said means for determining an optical eyeball model includes means for verifying validity of the optical eyeball model at an accommodation limit on a near point side and/or a far point side.

14. The system for determining an eyeglass/contact lens power according to claim 1, wherein said means for determining an optical eyeball model displays an image of the optical eyeball model determined.

15. The system for determining an eyeglass/contact lens power according to claim 1, wherein said means for selecting a lens power has a function to verify the focal power at a single distance or a plurality of distances defined according to usage.

16. The system for determining an eyeglass/contact lens power according to claim 1, wherein said means for selecting a lens power has a function to verify by comparison the focal power of the optical eyeball model for an uncorrected eye.

17. The system for determining an eyeglass/contact lens power according to claim 1, wherein said means for selecting a lens power includes means for calculating a sharpness score indicative of the degree of blurring in a visual image viewed by said optical eyeball model.

18. The system for determining an eyeglass/contact lens power according to claim 1, wherein said means for selecting a lens power includes means for presenting a simulated visual image viewed by said optical eyeball model.

19. The system for determining an eyeglass/contact lens power according to claim 1, wherein said means for determining an optical eyeball model has means for verifying validity of the optical eyeball model at a given accommodation point between said near point distance and said far point distance of the subject entered.

20. The system for determining an eyeglass/contact lens power according to claim 19, wherein said given accommodation point between the near point distance and the far point distance of the subject entered includes an accommodation midpoint calculated from the near point distance and the far point distance of the subject.

21. The system for determining an eyeglass/contact lens power according to claim 19, wherein said means for determining an optical eyeball model employs a radius of curvature and an eccentricity of an aspherical surface as parameters to perform automatic aberration correction processing.

22. A method for determining an eyeglass/contact lens power, comprising steps of:
collecting information on the conditions of an eye of a subject;
determining an optical eyeball model corresponding to the information on the conditions of the eye collected in said collecting step; and
selecting a lens power by verifying a focal power of an eyeglass/contact lens worn by the subject using the optical eyeball model determined in said step for determining an optical eyeball model.

23. The method for determining an eyeglass/contact lens power according to claim 22, wherein said collecting step includes a step of displaying an astigmatic axis measurement chart to measure an astigmatic axis.

24. The method for determining an eyeglass/contact lens power according to claim 22, wherein said collecting step includes a step of displaying a far point vision measurement chart to measure far point vision.

25. The method for determining an eyeglass/contact lens power according to claim 24, wherein said collecting step has a step of calculating a far point distance from said far point vision measured.

26. The method for determining an eyeglass/contact lens power according to claim 25, wherein said collecting step has a step of determining an approximate lens power from said far point distance calculated.

27. The method for determining an eyeglass/contact lens power according to claim 22, wherein said collecting step includes a step of displaying a near point distance measurement chart to measure a near point distance.

28. The method for determining an eyeglass/contact lens power according to claim 22 to, wherein said optical eyeball model simulates each layer of an anterior cortex, a nucleoplasm, and an posterior cortex of the lens of the eye using a combination of plurality of lenses, respectively.

29. The method for determining an eyeglass/contact lens power according to claim 28, wherein said optical eyeball model has a characteristic that a refractive index of each of said lenses simulating the lens of the eye is decreased with a distance from the center of the lens.

30. The method for determining an eyeglass/contact lens power according to claim 29, wherein said optical eyeball model has a refractive index distribution characteristic that the refractive index of each of said lenses simulating the lens of the eye is expressed by (a refractive index at the center of the lens)—((the square of a straight distance from the lens center)/(a refractive index distribution coefficient)).

31. The method for determining an eyeglass/contact lens power according to claim 28, wherein said refractive index distribution coefficient of each lens simulating the lens of the eye is decreased with the distance from the center of the plurality of lenses in a direction of the optical axis simulating the lens of the eye to the direction of the optical axis.

32. The method for determining an eyeglass/contact lens power according to claim 28, wherein said optical eyeball model calculates optical dimensions using a power distribution coefficient describing the distribution of accommodation power per unit length of each lens simulating the lens of the eye.

33. The method for determining an eyeglass/contact lens power according to claim 22, wherein said step of determining an optical eyeball model determines a starting optical eyeball model in accordance with an age of the subject and information on the eye such as an approximate lens power.

34. The method for determining an eyeglass/contact lens power according to claim 22, wherein said step of determining an optical eyeball model includes a step of verifying validity of the optical eyeball model at an accommodation limit on a near point side and/or a far point side.

35. The method for determining an eyeglass/contact lens power according to claim 22, wherein said step of determining an optical eyeball model displays an image of the optical eyeball model determined.

36. The method for determining an eyeglass/contact lens power according to claim 22, wherein said step of selecting a lens power has a step of verifying the focal power at a single distance or a plurality of distances defined according to usage.

37. The method for determining an eyeglass/contact lens power according to claim 22, wherein said step of selecting a lens power has a step of verifying by comparison the focal power of the optical eyeball model for an uncorrected eye.

38. The method for determining an eyeglass/contact lens power according to claim 22, wherein said step of selecting a lens power includes a step of calculating a sharpness score indicative of the degree of blurring in a visual image viewed by said optical eyeball model.

39. The method for determining an eyeglass/contact lens power according to claim 22 wherein said step of selecting a lens power includes a step of presenting a simulated visual image viewed by said optical eyeball model.

40. The method for determining an eyeglass/contact lens power according to claim 22, wherein said step of determining an optical eyeball model has a step of verifying validity of the optical eyeball model at a given accommodation point between said near point distance and said far point distance of the subject entered.

41. The method for determining an eyeglass/contact lens power according to claim 40, wherein said given accommodation point between the near point distance and the far point distance of the subject entered includes an accommodation midpoint calculated from the near point distance and the far point distance of the subject.

42. The method for determining an eyeglass/contact lens power according to claim 40, wherein said step of determining an optical eyeball model employs a radius of curvature and an eccentricity of an aspherical surface as parameters to perform automatic aberration correction processing.

* * * * *